(12) United States Patent
Cully et al.

(10) Patent No.: US 11,229,539 B2
(45) Date of Patent: Jan. 25, 2022

(54) EVERTABLE SHEATH DEVICES, SYSTEMS, AND METHODS

(71) Applicant: W. L. Gore & Associates, Inc., Newark, DE (US)

(72) Inventors: Edward H. Cully, Flagstaff, AZ (US); Craig W. Irwin, Parks, AZ (US); James D. Silverman, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 150 days.

(21) Appl. No.: 16/281,953

(22) Filed: Feb. 21, 2019

(65) Prior Publication Data
US 2019/0247210 A1 Aug. 15, 2019

Related U.S. Application Data

(62) Division of application No. 13/571,296, filed on Aug. 9, 2012, now Pat. No. 10,213,329.
(Continued)

(51) Int. Cl.
*A61F 2/958* (2013.01)
*A61F 2/966* (2013.01)
(Continued)

(52) U.S. Cl.
CPC ............ *A61F 2/958* (2013.01); *A61F 2/9526* (2020.05); *A61F 2/966* (2013.01); *A61F 2/9522* (2020.05); *A61F 2002/826* (2013.01)

(58) Field of Classification Search
CPC .. A61F 2/95; A61F 2/958; A61F 2/962; A61F 2/966; A61F 2002/826; A61F 2002/9583; A61F 2/9522
See application file for complete search history.

(56) References Cited

U.S. PATENT DOCUMENTS 4,553,545 A    11/1985  Maass et al.
4,732,152 A     3/1988  Wallsten et al.
(Continued)

FOREIGN PATENT DOCUMENTS

CN    102341145 A    2/2012
DE    19531659 A1    3/1997
(Continued)

OTHER PUBLICATIONS

Annex Form PCT/ISA/206 Communication Relating to the Results of the Partial International Search Report and Written Opinion for PCT/US2012/050272 dated Nov. 15, 2012, corresponding to U.S. Appl. No. 13/571,296.
(Continued)

*Primary Examiner* — Erich G Herbermann
*Assistant Examiner* — Christian D Knauss

(57) ABSTRACT

The present disclosure comprises devices, systems, and methods having an inverted sheath configured to cover, and in some instances constrain, a medical device and to retract through eversion, thus enabling the deployment of medical device at the treatment site. A constraining sheath can evert hydraulically. A constraining sheath can be configured to neck down a medical device to achieve a lower delivery profile. Furthermore, a constraining sheath can comprise a balloon to expand or positionally or structurally adjust a medical device.

15 Claims, 11 Drawing Sheets

Related U.S. Application Data

(60) Provisional application No. 61/523,186, filed on Aug. 12, 2011.

(51) Int. Cl.
*A61F 2/95* (2013.01)
*A61F 2/82* (2013.01)

(56) References Cited

U.S. PATENT DOCUMENTS

| | | | |
|---|---|---|---|
| 4,848,343 A * | 7/1989 | Wallsten | A61F 2/958 606/194 |
| 4,921,479 A | 5/1990 | Grayzel | |
| 5,064,435 A | 11/1991 | Porter | |
| 5,389,100 A | 2/1995 | Bacich et al. | |
| 5,425,765 A | 6/1995 | Tiefenbrun et al. | |
| 5,445,646 A | 8/1995 | Euteneuer et al. | |
| 5,571,135 A | 11/1996 | Fraser et al. | |
| 5,647,857 A | 7/1997 | Anderson et al. | |
| 5,662,703 A | 9/1997 | Yurek et al. | |
| 5,755,769 A | 5/1998 | Richard et al. | |
| 5,824,041 A | 10/1998 | Lenker et al. | |
| 5,989,280 A | 11/1999 | Euteneuer et al. | |
| 6,004,328 A * | 12/1999 | Solar | A61F 2/966 623/1.11 |
| 6,019,787 A | 2/2000 | Richard et al. | |
| 6,039,721 A | 3/2000 | Johnson et al. | |
| 6,042,605 A | 3/2000 | Martin et al. | |
| 6,059,813 A | 5/2000 | Vrba et al. | |
| 6,113,608 A | 9/2000 | Monroe et al. | |
| 6,203,550 B1 | 3/2001 | Olson | |
| 6,224,627 B1 | 5/2001 | Armstrong et al. | |
| 6,238,410 B1 | 5/2001 | Vrba et al. | |
| 6,254,628 B1 | 7/2001 | Wallace et al. | |
| 6,315,792 B1 | 11/2001 | Armstrong et al. | |
| 6,334,867 B1 | 1/2002 | Anson | |
| 6,350,278 B1 | 2/2002 | Lenker et al. | |
| 6,352,553 B1 | 3/2002 | Van et al. | |
| 6,352,561 B1 | 3/2002 | Leopold et al. | |
| 6,364,904 B1 | 4/2002 | Smith | |
| 6,383,171 B1 | 5/2002 | Gifford et al. | |
| 6,398,758 B1 | 6/2002 | Jacobsen et al. | |
| 6,524,335 B1 | 2/2003 | Hartley et al. | |
| 6,533,806 B1 | 3/2003 | Sullivan et al. | |
| 6,544,278 B1 | 4/2003 | Vrba et al. | |
| 6,607,552 B1 | 8/2003 | Hanson | |
| 6,645,242 B1 | 11/2003 | Quinn | |
| 6,733,521 B2 | 5/2004 | Chobotov et al. | |
| 6,790,225 B1 | 9/2004 | Shannon et al. | |
| 6,899,728 B1 | 5/2005 | Phillips et al. | |
| 6,911,039 B2 | 6/2005 | Shiu et al. | |
| 6,942,682 B2 | 9/2005 | Vrba et al. | |
| 6,949,112 B1 * | 9/2005 | Sridharan | A61L 29/06 606/194 |
| 6,974,471 B2 | 12/2005 | Van et al. | |
| 7,081,132 B2 | 7/2006 | Cook et al. | |
| 7,147,661 B2 | 12/2006 | Chobotov et al. | |
| 7,198,636 B2 | 4/2007 | Cully et al. | |
| 7,201,770 B2 | 4/2007 | Johnson et al. | |
| 7,285,130 B2 | 10/2007 | Austin | |
| 7,425,219 B2 | 9/2008 | Quadri | |
| 7,632,296 B2 | 12/2009 | Malewicz | |
| 7,645,298 B2 | 1/2010 | Hartley et al. | |
| 7,655,034 B2 | 2/2010 | Mitchell et al. | |
| 7,753,945 B2 | 7/2010 | Bruun et al. | |
| 7,794,488 B2 | 9/2010 | Vrba et al. | |
| 7,828,837 B2 | 11/2010 | Khoury | |
| 7,837,724 B2 | 11/2010 | Keeble et al. | |
| 7,938,851 B2 | 5/2011 | Olson et al. | |
| 7,955,370 B2 | 6/2011 | Gunderson | |
| 7,976,575 B2 | 7/2011 | Hartley | |
| 8,016,872 B2 | 9/2011 | Parker | |
| 8,147,538 B2 | 4/2012 | Brown et al. | |
| 8,167,926 B2 | 5/2012 | Hartley et al. | |
| 8,167,927 B2 | 5/2012 | Chobotov | |
| 8,231,665 B2 | 7/2012 | Kim et al. | |
| 8,241,346 B2 | 8/2012 | Chobotov | |
| 8,257,431 B2 | 9/2012 | Henderson et al. | |
| 8,262,671 B2 | 9/2012 | Osypka | |
| 8,317,854 B1 | 11/2012 | Ryan et al. | |
| 8,328,861 B2 | 12/2012 | Martin et al. | |
| 8,361,135 B2 | 1/2013 | Dittman | |
| 8,435,282 B2 | 5/2013 | Silverman | |
| 8,480,725 B2 | 7/2013 | Rasmussen et al. | |
| 8,540,760 B2 | 9/2013 | Paul et al. | |
| 8,641,752 B1 | 2/2014 | Holm et al. | |
| 8,764,816 B2 | 7/2014 | Koss et al. | |
| 8,801,774 B2 | 8/2014 | Silverman | |
| 8,845,712 B2 | 9/2014 | Irwin et al. | |
| 8,936,634 B2 | 1/2015 | Irwin et al. | |
| 8,968,384 B2 | 3/2015 | Pearson et al. | |
| 9,060,895 B2 | 6/2015 | Hartley et al. | |
| 9,114,037 B2 | 8/2015 | Silverman | |
| 9,132,025 B2 | 9/2015 | Aristizabal et al. | |
| 9,254,204 B2 | 2/2016 | Roeder et al. | |
| 9,308,349 B2 | 4/2016 | Rezac et al. | |
| 9,498,361 B2 | 11/2016 | Roeder et al. | |
| 9,526,641 B2 | 12/2016 | Irwin et al. | |
| 9,585,743 B2 | 3/2017 | Cartledge et al. | |
| 9,585,774 B2 | 3/2017 | Aristizabal et al. | |
| 9,668,853 B2 | 6/2017 | Shin | |
| 9,681,968 B2 | 6/2017 | Goeiz et al. | |
| 9,700,701 B2 | 7/2017 | Benjamin et al. | |
| 9,763,819 B1 | 9/2017 | Sondreaal | |
| 9,782,284 B2 | 10/2017 | Hartley et al. | |
| 9,907,641 B2 | 3/2018 | Johnson | |
| 9,937,070 B2 | 4/2018 | Skelton et al. | |
| 10,213,329 B2 | 2/2019 | Cully et al. | |
| 10,405,966 B2 | 9/2019 | Johnson | |
| 2001/0044595 A1 | 11/2001 | Reydel et al. | |
| 2001/0056295 A1 | 12/2001 | Solem | |
| 2002/0002397 A1 | 1/2002 | Martin et al. | |
| 2002/0038141 A1 | 3/2002 | Yang et al. | |
| 2002/0099431 A1 | 7/2002 | Armstrong et al. | |
| 2002/0138129 A1 | 9/2002 | Armstrong et al. | |
| 2003/0004561 A1 | 1/2003 | Bigus et al. | |
| 2003/0105508 A1 | 6/2003 | Johnson et al. | |
| 2003/0135258 A1 | 7/2003 | Andreas et al. | |
| 2003/0176910 A1 | 9/2003 | Vrba et al. | |
| 2003/0199966 A1 | 10/2003 | Shiu et al. | |
| 2003/0199967 A1 | 10/2003 | Hartley et al. | |
| 2003/0212410 A1 | 11/2003 | Stenzel et al. | |
| 2004/0087886 A1 | 5/2004 | Gellman | |
| 2004/0092977 A1 | 5/2004 | Vargas et al. | |
| 2004/0143272 A1 | 7/2004 | Cully et al. | |
| 2004/0143315 A1 | 7/2004 | Bruun et al. | |
| 2004/0211433 A1 | 10/2004 | Leland | |
| 2005/0049675 A1 | 3/2005 | Wallace | |
| 2005/0059923 A1 | 3/2005 | Gamboa | |
| 2005/0165352 A1 | 7/2005 | Henry et al. | |
| 2005/0240254 A1 | 10/2005 | Austin | |
| 2006/0015135 A1 | 1/2006 | Vrba et al. | |
| 2006/0015171 A1 | 1/2006 | Armstrong | |
| 2006/0030923 A1 | 2/2006 | Gunderson | |
| 2006/0030924 A1 | 2/2006 | Van et al. | |
| 2006/0041302 A1 | 2/2006 | Malewicz | |
| 2006/0089627 A1 | 4/2006 | Burnett et al. | |
| 2006/0122685 A1 | 6/2006 | Bonsignore et al. | |
| 2006/0173422 A1 | 8/2006 | Reydel et al. | |
| 2006/0184226 A1 | 8/2006 | Austin | |
| 2006/0200221 A1 | 9/2006 | Malewicz | |
| 2006/0206123 A1 | 9/2006 | Brenneman | |
| 2007/0055358 A1 | 3/2007 | Krolik et al. | |
| 2007/0060999 A1 | 3/2007 | Randall et al. | |
| 2007/0093886 A1 | 4/2007 | Cully et al. | |
| 2007/0142904 A1 | 6/2007 | Sorenson et al. | |
| 2007/0191925 A1 | 8/2007 | Dorn | |
| 2007/0208350 A1 * | 9/2007 | Gunderson | A61F 2/95 606/108 |
| 2007/0219612 A1 | 9/2007 | Andreas et al. | |
| 2007/0244540 A1 | 10/2007 | Pryor | |
| 2008/0140003 A1 | 6/2008 | Bei et al. | |
| 2008/0140173 A1 * | 6/2008 | Eskaros | A61M 25/1029 623/1.11 |

(56) References Cited

U.S. PATENT DOCUMENTS

| | | |
|---|---|---|
| 2008/0167705 A1 | 7/2008 | Agnew |
| 2008/0255580 A1 | 10/2008 | Hoffman et al. |
| 2008/0281398 A1 | 11/2008 | Koss et al. |
| 2009/0018501 A1 | 1/2009 | Yribarren et al. |
| 2009/0099638 A1 | 4/2009 | Grewe |
| 2009/0125093 A1 | 5/2009 | Hansen |
| 2009/0143713 A1 | 6/2009 | Van et al. |
| 2009/0182411 A1* | 7/2009 | Irwin ................ A61F 2/97 623/1.12 |
| 2009/0192584 A1 | 7/2009 | Gerdts et al. |
| 2009/0254063 A1 | 10/2009 | Oepen et al. |
| 2009/0270969 A1 | 10/2009 | Fargahi et al. |
| 2009/0299449 A1 | 12/2009 | Styrc |
| 2009/0326449 A1 | 12/2009 | Wang et al. |
| 2010/0004606 A1 | 1/2010 | Hansen et al. |
| 2010/0023106 A1 | 1/2010 | Meyer et al. |
| 2010/0036360 A1 | 2/2010 | Herbowy et al. |
| 2010/0036472 A1 | 2/2010 | Papp |
| 2010/0069852 A1 | 3/2010 | Kelley |
| 2010/0094398 A1 | 4/2010 | Malewicz |
| 2010/0100170 A1 | 4/2010 | Tan et al. |
| 2010/0168835 A1 | 7/2010 | Dorn |
| 2010/0234933 A1 | 9/2010 | Punga et al. |
| 2010/0331955 A1 | 12/2010 | Vrba et al. |
| 2011/0009943 A1 | 1/2011 | Paul et al. |
| 2011/0015716 A1 | 1/2011 | Silverman |
| 2011/0022154 A1 | 1/2011 | Hamer et al. |
| 2011/0034987 A1 | 2/2011 | Kennedy |
| 2011/0118765 A1 | 5/2011 | Aguirre |
| 2011/0118817 A1 | 5/2011 | Gunderson et al. |
| 2011/0137401 A1 | 6/2011 | Dorn et al. |
| 2011/0137402 A1 | 6/2011 | Dorn et al. |
| 2011/0166637 A1 | 7/2011 | Irwin et al. |
| 2011/0208292 A1 | 8/2011 | Von et al. |
| 2012/0016454 A1 | 1/2012 | Jantzen et al. |
| 2012/0059448 A1 | 3/2012 | Parker et al. |
| 2012/0078343 A1 | 3/2012 | Fish |
| 2012/0120287 A1 | 5/2012 | Funamoto et al. |
| 2012/0130472 A1 | 5/2012 | Shaw |
| 2012/0130473 A1 | 5/2012 | Norris et al. |
| 2012/0130474 A1 | 5/2012 | Buckley |
| 2012/0143306 A1 | 6/2012 | Cully et al. |
| 2012/0165915 A1 | 6/2012 | Melsheimer et al. |
| 2012/0193018 A1 | 8/2012 | Banas et al. |
| 2012/0239134 A1 | 9/2012 | Dierking |
| 2012/0296406 A1 | 11/2012 | Minion |
| 2012/0296412 A1 | 11/2012 | Paul et al. |
| 2012/0323315 A1 | 12/2012 | Bruchman et al. |
| 2013/0006220 A1 | 1/2013 | Yribarren et al. |
| 2013/0035749 A1 | 2/2013 | Farag |
| 2013/0150949 A1 | 6/2013 | Silverman |
| 2013/0158524 A1 | 6/2013 | Fargahi |
| 2013/0204343 A1 | 8/2013 | Shalev |
| 2013/0204345 A1 | 8/2013 | Cully et al. |
| 2013/0211493 A1 | 8/2013 | Wubbeling et al. |
| 2013/0238080 A1 | 9/2013 | Silverman |
| 2013/0245742 A1 | 9/2013 | Norris |
| 2013/0274851 A1 | 10/2013 | Kelly |
| 2013/0296877 A1 | 11/2013 | Rwin et al. |
| 2013/0340233 A1 | 12/2013 | Tollner et al. |
| 2014/0081376 A1 | 3/2014 | Burkart et al. |
| 2014/0130475 A1 | 5/2014 | Van et al. |
| 2014/0135895 A1 | 5/2014 | Andress et al. |
| 2014/0358156 A1 | 12/2014 | Argentine |
| 2015/0134043 A1 | 5/2015 | Irwin et al. |
| 2015/0196383 A1 | 7/2015 | Johnson |
| 2015/0250630 A1 | 9/2015 | Irwin et al. |
| 2016/0045349 A1 | 2/2016 | Kilgrow et al. |
| 2017/0172724 A1 | 6/2017 | Cartledge et al. |
| 2017/0281382 A1 | 10/2017 | Lostetter et al. |
| 2019/0247210 A1 | 8/2019 | Cully et al. |
| 2020/0022800 A1 | 1/2020 | Johnson |
| 2020/0323670 A1 | 10/2020 | Honeyfield et al. |
| 2021/0186725 A1 | 6/2021 | Irwin et al. |

FOREIGN PATENT DOCUMENTS

| | | |
|---|---|---|
| EP | 1779809 A1 | 5/2007 |
| EP | 1441668 B1 | 1/2008 |
| EP | 1915113 B1 | 3/2010 |
| EP | 2175813 A1 | 4/2010 |
| EP | 2352464 A1 | 8/2011 |
| EP | 1358903 B1 | 11/2011 |
| EP | 2491894 A1 | 8/2012 |
| EP | 1474074 B1 | 4/2014 |
| EP | 2749251 B1 | 7/2016 |
| EP | 2956198 B1 | 11/2017 |
| JP | 2000-279532 A | 10/2000 |
| JP | 2002-518086 A | 6/2002 |
| JP | 2002-537026 A | 11/2002 |
| JP | 2006-006648 A | 1/2006 |
| JP | 2007-534441 A | 11/2007 |
| JP | 2010-526583 A | 8/2010 |
| JP | 2011-509744 A | 3/2011 |
| JP | 2017-511725 A | 4/2017 |
| WO | 98/08456 A1 | 3/1998 |
| WO | 98/26731 A2 | 6/1998 |
| WO | 99/65420 A1 | 12/1999 |
| WO | 00/48645 A2 | 8/2000 |
| WO | 01/01886 A1 | 1/2001 |
| WO | 01/22903 A2 | 4/2001 |
| WO | 02/38084 A2 | 5/2002 |
| WO | 2005/107644 A1 | 11/2005 |
| WO | 2008/034793 A1 | 3/2008 |
| WO | 2008/137177 A2 | 11/2008 |
| WO | 2009/012061 A1 | 1/2009 |
| WO | 2009/091603 A1 | 7/2009 |
| WO | 2009/145901 A1 | 12/2009 |
| WO | 2010/063794 A1 | 6/2010 |
| WO | 2010/063795 A1 | 6/2010 |
| WO | 2010/120671 A1 | 10/2010 |
| WO | 2011/076408 A1 | 6/2011 |
| WO | 2012/054178 A1 | 4/2012 |
| WO | 2013/025470 A2 | 2/2013 |

OTHER PUBLICATIONS

International Preliminary Report on Patentability received for PCT Patent Application No. PCT/US2012/050272, dated Feb. 27, 2014, 12 pages.

International Search Report and Written Opinion received for PCT Patent Application No. PCT/US2012/050272, dated Feb. 21, 2013, 18 pages.

International Preliminary Reporton Patentability received for PCT Patent Application No. PCT/US2018/055223, dated Apr. 23, 2020, 9 pages.

Invitation to Pay Additional Fees received for PCT Patent Application No. PCT/US2018/055223, dated Dec. 21, 2018, 8 pages.

* cited by examiner

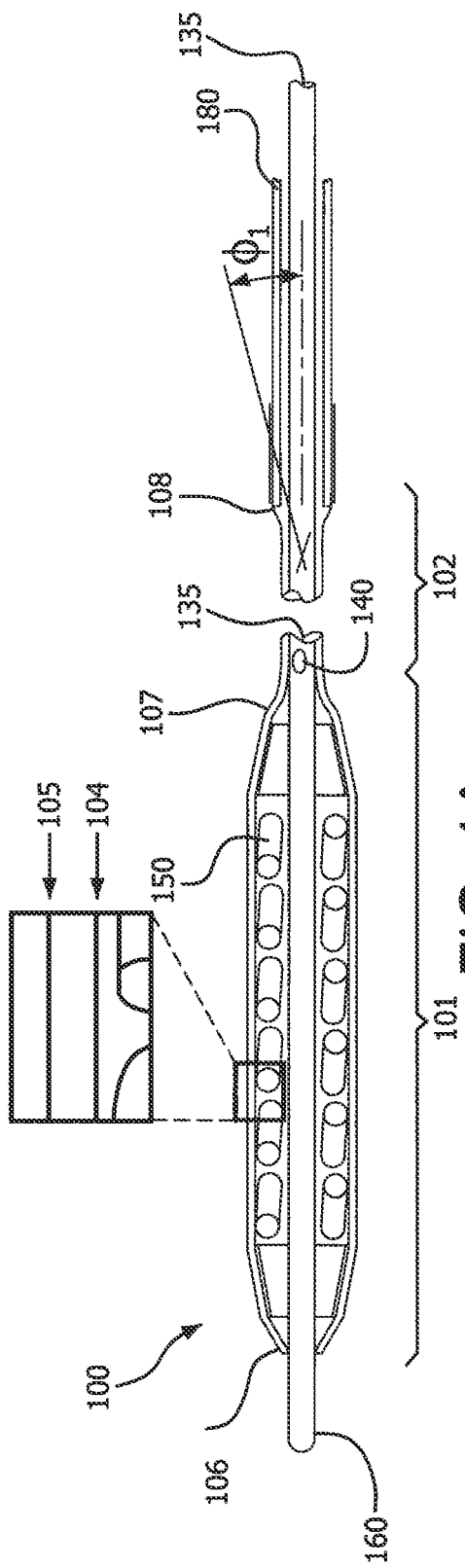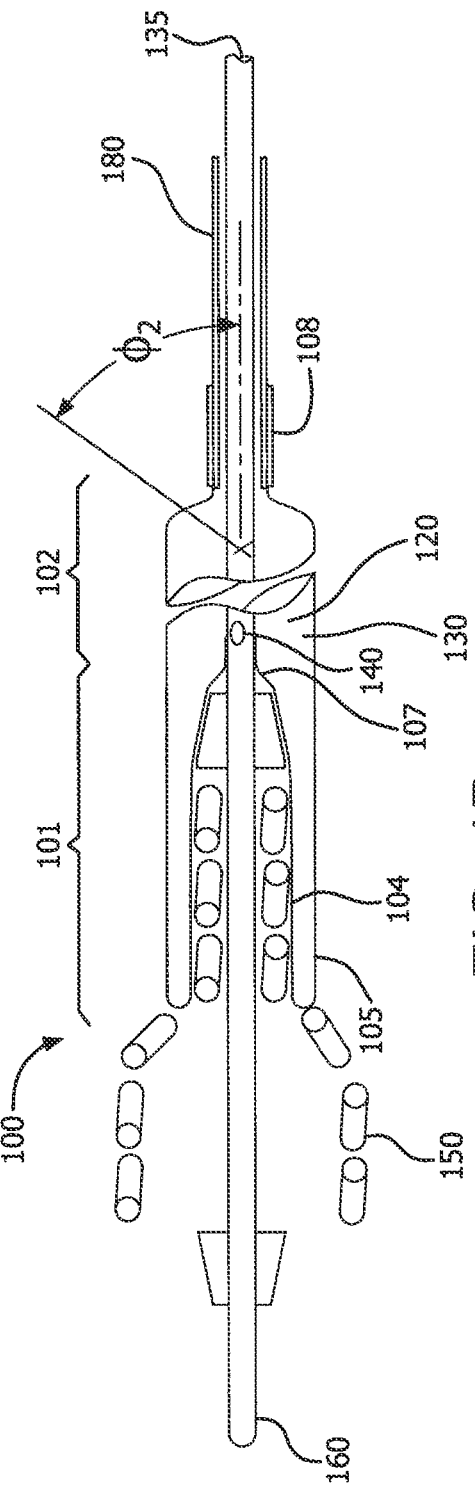
FIG. 1A
FIG. 1B

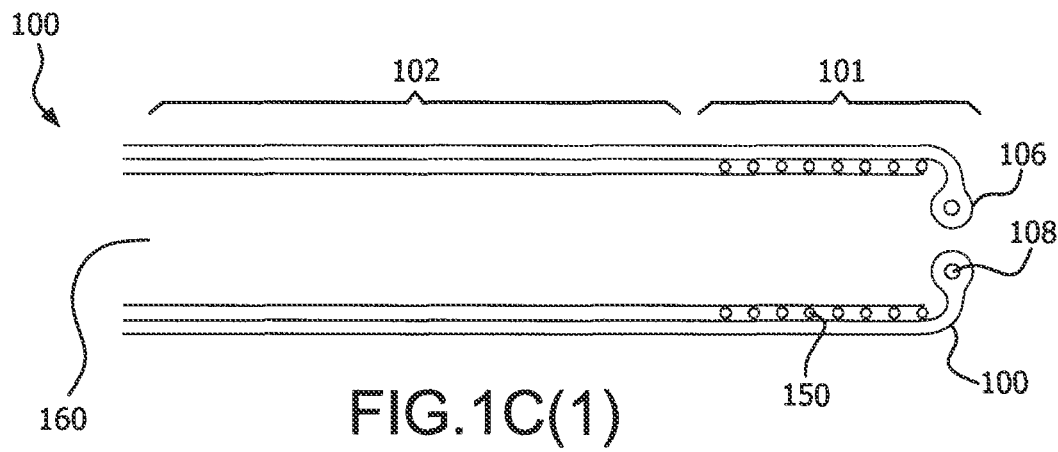
FIG.1C(1)
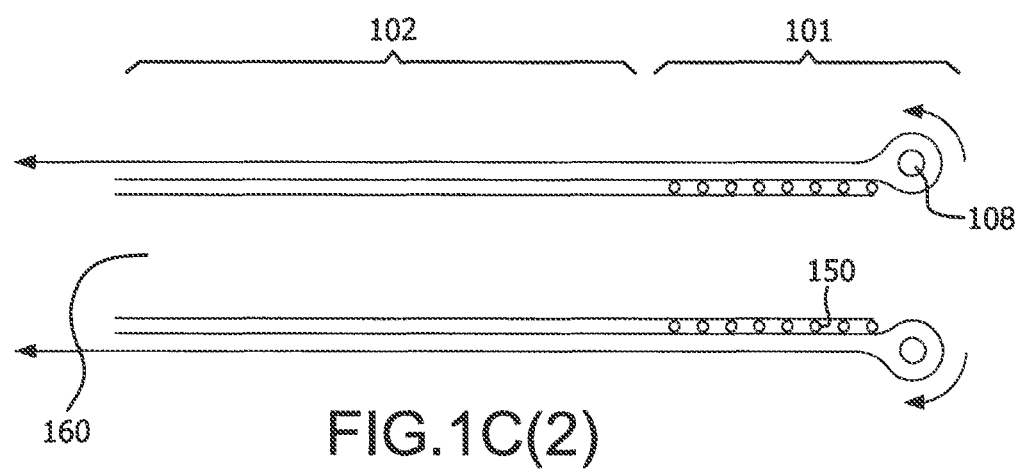
FIG.1C(2)
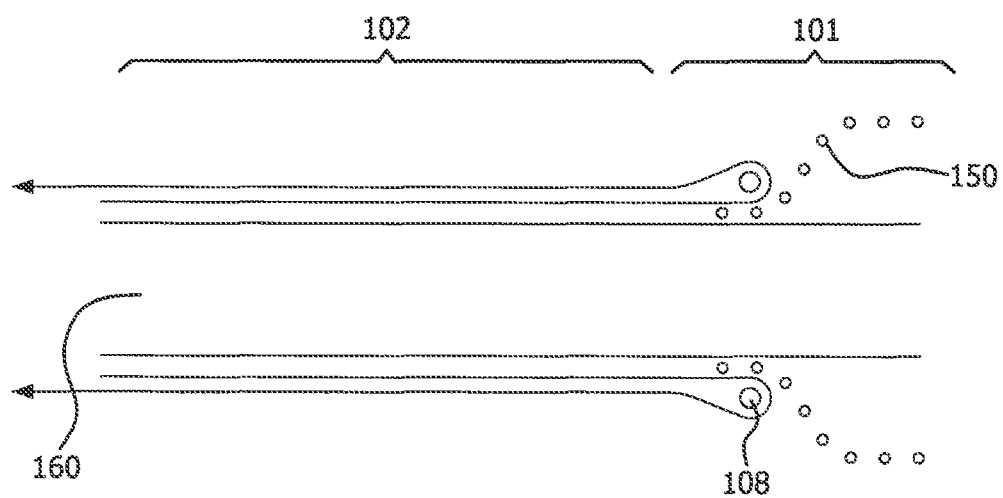
FIG.1C(3)

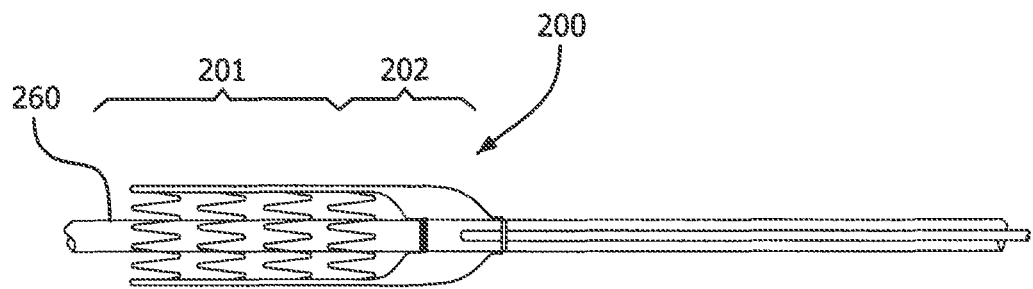
FIG. 2A
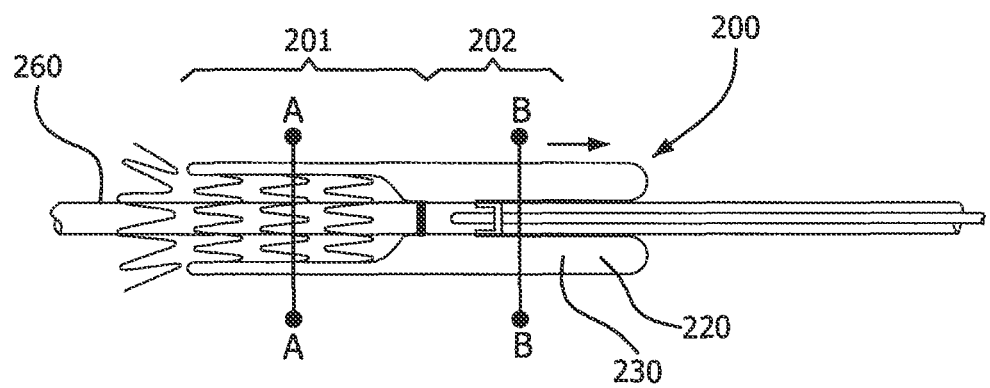
FIG. 2B
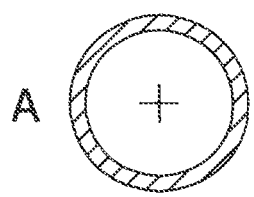 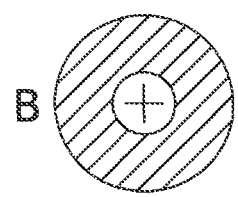
FIG. 2C      FIG. 2D

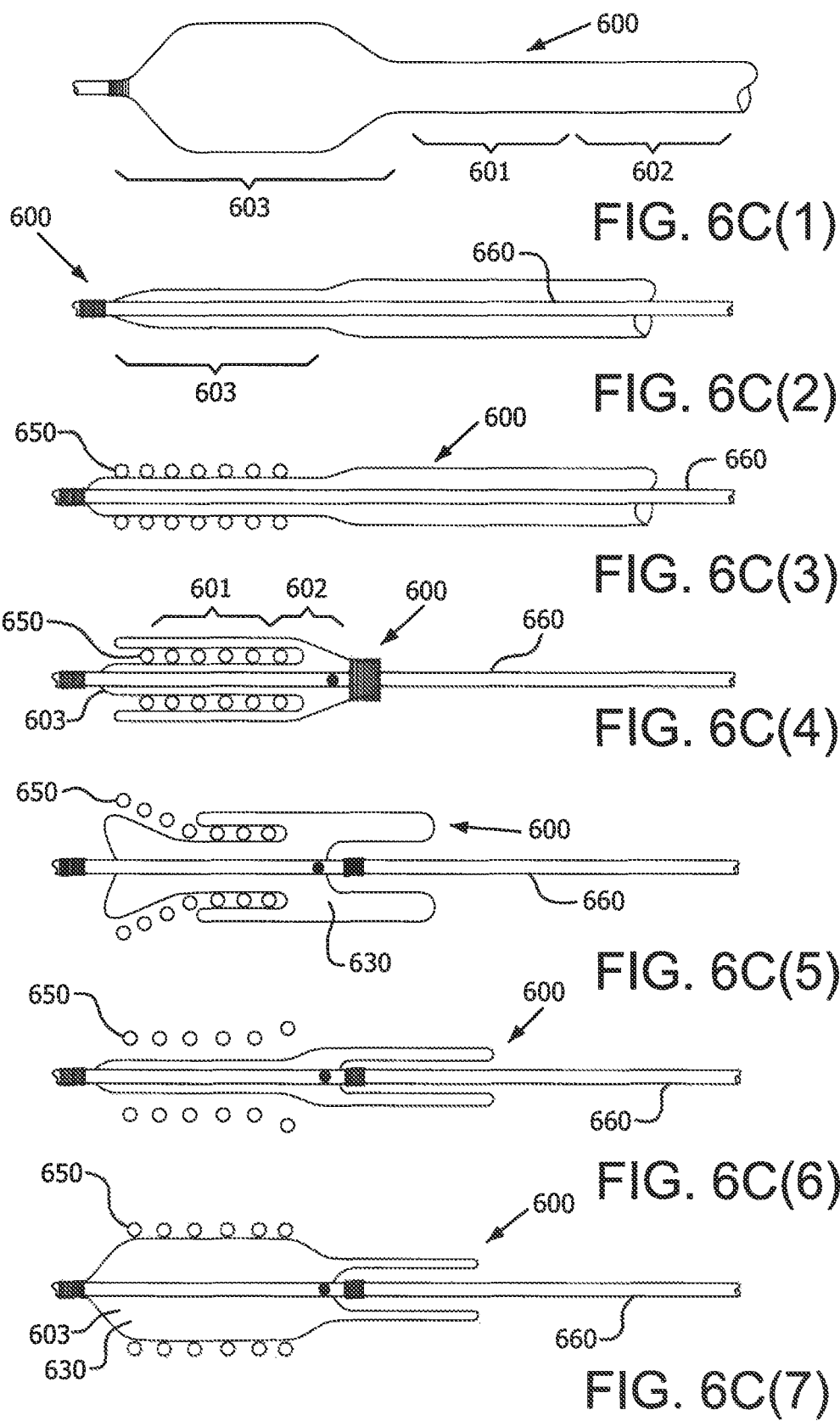

EVERTABLE SHEATH DEVICES, SYSTEMS, AND METHODS

CROSS-REFERENCE TO RELATED APPLICATION

This application is a divisional of U.S. patent application Ser. No. 13/571,296, filed Aug. 9, 2012, which claims the benefit of U.S. Provisional No. 61/523,186, filed on Aug. 12, 2011, both of which are hereby incorporated by reference in their entireties for all purposes.

BACKGROUND OF THE DISCLOSURE

Field of the Disclosure

The present disclosure relates to a delivery and deployment devices, systems, and methods, more specifically to intraluminal and endovascular delivery and deployment devices, systems, and methods.

Discussion of the Related Art

Intraluminal and endovascular procedures provide many advantages over surgery, so much so that when intraluminal or endovascular treatment is an option, it is usually the preferred option. This preference arises from the fact that such procedures are minimally invasive methods of treating diseases. Benefits of minimally invasive procedures include more rapid procedures, shorter hospital stays, quicker recoveries, and lower risk of complications. Thus, expanding the number of procedures that can be performed intraluminally or endovascularly is a widely advantageous endeavor.

However, expanding the number of procedures that can be performed intraluminally or endovascularly requires improving the ability to deliver and deploy a device and/or treatment from a remote location, typically a location outside the body. To improve delivery, the lowest possible delivery profile is preferred to introduce into a vessel and traverse irregularly shaped, highly tortuous, heavily branched, and very narrow lumens or vessels to gain access to the treatment site. Obtaining a small delivery profile requires that the medical device be collapsed and constrained, typically onto a catheter. This is achieved by using a constraining device to hold the medical device in a collapsed and compressed configuration. However, deploying a constrained medical device presents additional issues.

Loading the medical device onto the catheter and into the constraint, to achieve the low profile, subjects the device to frictional forces, which may cause damage to the medical device. Frictional forces may also produce strain in the deployment system, impeding a stable, controlled deployment. Frictional force challenges are especially prevalent in deployment systems which employ a sliding sheath positioned external to the device and in braid and knit braid constraints. They are also of concern in systems using long catheters and those with constraints on or over long devices, both of which increase deployment friction. Typically, achieving a lower profile means increasing frictional forces and exacerbating the adverse effects associated therewith. As a result, the frictional forces limit, amongst other things, the types and dimensions of devices and treatments that can be deployed or administered endovascularly or intraluminally.

Therefore, there exists a need for a delivery and deployment device that can deploy a device or treatment in a stable, controlled manner with less friction and do so while maintaining or decreasing the delivery profile.

SUMMARY OF THE DISCLOSURE

Embodiments of the present disclosure are directed toward an apparatus, system, and method for endovascular or intraluminal delivery and deployment of a medical device. The present disclosure is directed toward constraining sheath designs or modifications that, inter alia, reduce the degree of friction associated with loading and deploying a medical device, that lower delivery profile (e.g., <7 Fr.), and that stabilize the deployment of the medical device, which improves a clinician's ability to accurately position and deploy medical devices, especially those which are relatively long (e.g., >25 cm) or those with aspect ratios in which lengths are short and diameters large.

According to one aspect of the disclosure, constraining sheath comprises an evertable constraining sheath. An evertable constraining sheath comprises an inverted sheath configured to at least partially cover, and in some instances constrain, a medical device and to retract through eversion, thus enabling the deployment of medical device at the treatment site. A constraining sheath can evert through any number of mechanisms which can cause foreshortening and/or axial displacement of the sheath. Fluid can be introduced into the sheath to reduce friction during eversion. In addition, in some embodiments, the hydraulic pressure created by fluid introduction can also cause foreshortening and/or axial displacement. Retracting a sheath can also occur, in whole or in part, via a retracting member or the radial expansion of a medical device constrained or covered by the sheath.

In addition, a constraining sheath can be configured to "neck down" or decrease in diameter upon elongation (e.g., the application of axial force) to constrain a medical device to achieve a lower delivery profile. Furthermore, a constraining sheath can comprise a balloon to facilitate contact with the surrounding tissue and/or to expand or adjust the position or structure of a medical device during or following deployment.

Other aspects of the disclosure comprise deployment systems having an inverted sheath covering and optionally constraining medical device, as well as methods of covering a medical device with an inverted sheath onto a catheter and then deploying that medical device constrained by the inverted sheath through eversion.

Similarly, another aspect of the disclosure comprises deployment systems having an inverted sheath and medical device loaded onto a catheter, as well as methods of loading a medical device and an inverted sheath onto a catheter and then deploying that medical device constrained by the inverted sheath through eversion.

BRIEF DESCRIPTION OF THE DRAWINGS

The accompanying drawings are included to provide a further understanding of the disclosure and are incorporated in and constitute a part of this specification, illustrate embodiments of the disclosure and, together with the description, serve to explain the principles of the disclosure.

FIGS. 1A-1B illustrate a cross-sectional view of an evertable sheath embodiment constraining a medical device loaded onto an elongate member;

FIGS. 1C(1) to 1C(3) illustrate a cross-sectional view of an evertable sheath embodiment having a restraining member and undergoing eversion, thereby releasing a constrained medical device;

FIGS. 2A-2B illustrate a cross-sectional view of an evertable sheath embodiment in a rolling configuration constraining a medical device loaded onto an elongate member;

FIG. 2C illustrates a cross-sectional view of the evertable sheath embodiment along line A-A in FIG. 2B.

FIG. 2D illustrates a cross-sectional view of the evertable sheath embodiment along line B-B in FIG. 2B;

FIGS. 6C(1)-(7) illustrate a variety of cross-sectional views of an exemplary evertable sheath comprising a balloon portion;

DETAILED DESCRIPTION OF THE ILLUSTRATED EMBODIMENTS

Figure 1D:
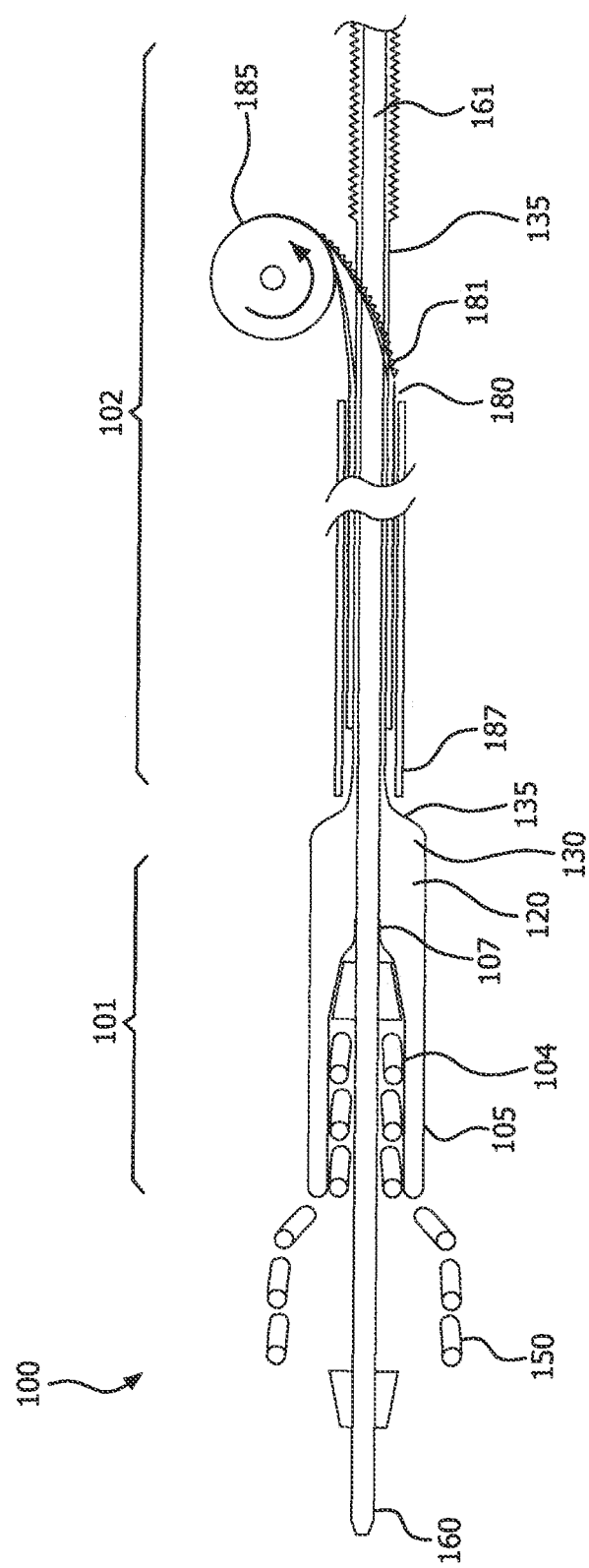
FIG. 1D illustrates a cross-sectional view of an evertable sheath embodiment having a coaxial housing and a retraction wheel and undergoing eversion, thereby releasing a constrained a medical device.

Persons skilled in the art will readily appreciate that various aspects of the present disclosure can be realized by any number of methods and apparatuses configured to perform the intended functions. Stated differently, other methods and apparatuses can be incorporated herein to perform the intended functions. It should also be noted that the accompanying drawing figures referred to herein are not all drawn to scale, but can be exaggerated to illustrate various aspects of the present disclosure, and in that regard, the drawing figures should not be construed as limiting.

Although the present disclosure can be described in connection with various principles and beliefs, the present disclosure should not be bound by theory. For example, the present disclosure is described herein in connection with intraluminal and endovascular treatments, specifically the delivery and deployment of intraluminal prostheses or endoprostheses and endo- or intraluminal drug delivery devices. However, the present disclosure can be applied toward any delivering or deployment mechanism of similar structure and/or function. Furthermore, the present disclosure can be applied in non-endovascular applications, and even non-biologic and non-medical applications.

Embodiments of the present disclosure are directed toward an apparatus, system, and method for intraluminal or endovascular delivery and deployment of a medical device. Constraining sheath designs or modifications described herein can reduce the degree of friction associated with loading and deploying a medical device. In addition, constraining sheath designs or modifications can be useful toward obtaining a low delivery profile (e.g., <7 Fr.) and smooth crossing topography. Reduced delivery profiles and smooth crossing profiles allow for an improved range of access to treatment sites as well as reduced vascular access incision size. In another aspect, constraining sheath designs or modifications can stabilize the deployment of the medical device through uniform loading and retraction, which improves a clinician's ability to accurately position and deploy medical devices, especially those which are relatively long (e.g., >25 cm) or those with aspect ratios in which lengths are short and diameters large. Lastly, the present disclosure is directed toward a constraining sheath that does not slide against a medical device during deployment, thus providing the ability to deploy medical devices with outer structural features that would otherwise interfere with such sheath retraction, e.g., anchors, coatings (e.g., drug coatings) or other protruding features.

A constraining sheath, as used herein, is a device configured to cover or constrain a device, such as a medical device for intraluminal or endovascular delivery and deployment. As used in the context of medical devices, a constraining sheath can surround or envelop at least part of a medical device. Typically, an endoluminal medical device will be in a collapsed configuration, and a sheath will closely fit around the collapsed medical device. In various embodiments, the medical device is mounted onto or otherwise positioned on an elongate member, such as a catheter, or located just beyond the distal end of elongate member, in order to be transported through the vasculature to a deployment site. Once the medical device reaches a deployment site, the constraining sheath is removed to facilitate a treatment outcome.

A constraining sheath, in accordance with a present disclosure, comprises an evertable constraining sheath. Evertable constraining sheaths comprise any sheath configured to cover, and in some instances constrain, a medical device and to retract through eversion, thus enabling the deployment of the medical device at the treatment site. (As used herein, "eversion" and variations thereof comprise motion wherein an inner portion is turned outward.) Importantly, the medical device can be, but is not necessarily, constrained by the constraining sheath of the present disclosure. Stated differently, the constraining sheath of the present disclosure can serve merely as a cover.

Evertable constraining sheaths can be configured to retract in a distal to proximal direction, proximal to distal direction, or both. In various embodiments, a constraining sheath can evert, in whole or in part, by foreshortening. As used herein, to "foreshorten" is to reduce the length of a material or form. Foreshortening can be actuated by increasing one or more sheath profiles, from a first profile to a second profile. Increases in the profile can occur by introducing a fluid in between inner and outer walls of a sheath, i.e., hydraulic increases in profile, resulting in hydraulic eversion. Among others, fluid, as described infra, can include a liquid, gel or a gas.

In same or different embodiments, eversion of the constraining sheath can be facilitated, in whole or in part, via axial displacement. In some embodiments, axial displacement of a retracting member, which can be coupled to or integral with the constraining sheath, causes axial displacement of the constraining sheath. Similarly, in same or different embodiments, increasing to the second profile, e.g., via hydraulic pressure, can facilitate axial displacement. Another mode of eversion comprising the constraining sheath can be facilitated via the radial pressure applied by an expanding medical device. In these various embodiments, introduction of the fluid can serve to reduce the friction between the inner and outer walls of sheath and thereby reduce the forces required to cause eversion.

In addition, in same or different embodiments, an evertable constraining sheath can be configured to neck down around the constrained medical device and further reduce the profile. During or after the constraining of a medical device by the evertable constraining sheath, tension can be applied to reduce the diameter and/or width of the sheath which in turn further reduces the profile of the loaded system overall. As stated above, delivery profiles less than 7 Fr. can be achieved for certain devices. Reductions in profile can be realized when comparing the profile of the evertable sheath with and without necking.

A medical device, in accordance with a present disclosure, comprises any medical device that can be covered or constrained with a sheath and delivered intraluminally or endovascularly. For example, a stent or stent graft, when implanted endovascularly, must be constrained to a low delivery profile in order to gain access to the treatment site. Similarly, grafts, filters, valves, bifurcated stents, anchors, occluders, drug-delivering devices (e.g., drug coated or drug-eluting balloons and stents), indwelling catheters, oncology therapies, pressure flow monitors, energy transmission devices, or other similar devices can also be covered with a sheath and delivered endovascularly or intraluminally. Medical devices can be balloon expandable or self-expanding or a combination of both. In addition, multiple devices, positioned on an elongate member, can be sequentially deployed. In the case of devices that deliver a drug or other therapeutic agent, the covering can also ensure that minimal drug is released into the bloodstream prior to deployment and during deployment.

Once the medical device reaches the treatment site, the sheath is then everted to uncover the medical device. In the case of a self-expanding medical device, the medical device will deploy as the sheath is everted. In the case of a balloon-expanding device, the medical device will not deploy until a balloon is inflated. The balloon can be inflated concurrently with or subsequent to the eversion of the sheath. As will be described below, immediate, sequential inflation and eversion can be conducted in a manner to improve the stability of the deployment.

As used herein, an "elongate member" is a flexible element having proximal and distal ends and capable of extending through a vessel. Elongate member can be configured to be bendable to traverse through tortuous vasculature, and can further be configured to minimize or eliminate kinking. Elongate member can comprise an outer diameter of sufficient size to permit passage through vasculature to access a treatment site. Examples include a guidewire, catheter, optical fiber, or the like. An elongate member can further include any longitudinally extending structure with or without a lumen there through. Thus, elongate members include but are not limited to tubes with lumens, solid rods, hollow or solid wires (e.g., guidewires), hollow or solid stylets, metal tubes (e.g., hypotubes), polymer tubes, pull cords or tethers, fibers, filaments, electrical conductors, radiopaque elements, radioactive elements and radiographic elements. Elongate member can comprise a blunt, rounded, or tapered distal tip, to name a few, and can be characterized by varying degrees of rigidity or softness, which can further vary along the length of the elongate member. Elongate members can have any cross-sectional shape including circular, oval, triangular, square, polygon shaped or randomly shaped. An elongate member, or any portion thereof, can be hydrophilic or hydrophobic.

Elongate member can comprise any medical-grade material. Elongate member can comprise polymeric or metallic materials or combinations thereof. For example, elongate member can comprise a polymeric film tube with spiral or braided nitinol reinforcements. Typical materials used to construct an elongate member comprise commonly known materials such as Amorphous Commodity Thermoplastics that include Polymethyl Methacrylate (PMMA or Acrylic), Polystyrene (PS), Acrylonitrile Butadiene Styrene (ABS), Polyvinyl Chloride (PVC), Modified Polyethylene Terephthalate Glycol (PETG), Cellulose Acetate Butyrate (CAB); Semi-Crystalline Commodity Plastics that include Polyethylene (PE), High Density Polyethylene (HDPE), Low Density Polyethylene (LDPE or LLDPE), Polypropylene (PP), Polymethylpentene (PMP); Amorphous Engineering Thermoplastics that include Polycarbonate (PC), Polyphenylene Oxide (PPO), Modified Polyphenylene Oxide (Mod PPO), Polyphenylene Ether (PPE), Modified Polyphenylene Ether (Mod PPE), Thermoplastic Polyurethane (TPU); Semi-Crystalline Engineering Thermoplastics that include Polyamide (PA or Nylon), Polyoxymethylene (POM or Acetal), Polyethylene Terephthalate (PET, Thermoplastic Polyester), Polybutylene Terephthalate (PBT, Thermoplastic Polyester), Ultra High Molecular Weight Polyethylene (UHMW-PE); High Performance Thermoplastics that include Polyimide (PI, Imidized Plastic), Polyamide Imide (PAI, Imidized Plastic), Polybenzimidazole (PBI, Imidized Plastic); Amorphous High Performance Thermoplastics that include Polysulfone (PSU), Polyetherimide (PEI), Polyether Sulfone (PES), Polyaryl Sulfone (PAS); Semi-Crystalline High Performance Thermoplastics that include Polyphenylene Sulfide (PPS), Polyetheretherketone (PEEK); and Semi-Crystalline High Performance Thermoplastics, Fluoropolymers that include Fluorinated Ethylene Propylene (FEP), Ethylene Chlorotrifluroethylene (ECTFE), Ethylene, Ethylene Tetrafluoroethylene (ETFE), Polychlortrifluoroethylene (PCTFE), Polytetrafluoroethylene (PTFE), expanded Polytetrafluoroethylene (ePTFE), Polyvinylidene Fluoride (PVDF), Perfluoroalkoxy (PFA). Other commonly known medical grade materials include elastomeric organosilicon polymers, polyether block amide or thermoplastic copolyether (PEBAX) and metals such as stainless steel and nickel/titanium alloys.

With reference now to FIGS. 1A-1B, an evertable constraining sheath, in accordance with a present disclosure, comprises an at least partially inverted sheath 100 configured to cover, and in some instances constrain, a medical device 150 and to retract through eversion, thereby enabling the deployment of medical device 150 at the treatment site. Inverted sheath 100 can be configured to evert in a distal to proximal direction, proximal to distal direction, or both. Furthermore, inverted sheath 100 can be configured to evert via axial displacement and/or foreshortening, which can be caused by application of a pressure, e.g., a hydraulic pressure.

In an embodiment, inverted sheath 100 comprises an inverted portion 101 configured to cover or constrain medical device 150, e.g., a stent as shown. The inverted portion 101 can radially compress or cover medical device 150 in a substantially uniform manner along a substantial length and circumference of medical device 150. Inverted portion 101 everts and thereby retracts sheath 100 from medical device 150. In various embodiments, inverted sheath 100 can further comprise a neck portion 102. Neck portion 102 comprises portion of inverted sheath 100 that does not circumscribe medical device 150.

In various embodiments, to facilitate eversion, inverted sheath 100 can transition from a first profile to a second profile. FIG. 1A depicts an embodiment of an inverted sheath in a first profile. FIG. 1B depicts an embodiment of an inverted sheath in a second profile. As used herein, a "profile" comprises any of the following: sheath width, diameter, volume, cross-sectional area, or the like. Profiles may be different along a dimension of sheath 100, e.g., its longitudinal dimension. To facilitate eversion, inverted sheath 100 transitions from a first profile to a second profile to create foreshortening and/or axial displacement. The transition from the first profile to the second profile occurs by the application of a force (e.g., an internal hydraulic pressure) to create a clearance between inner and outer walls of sheath 100 or between walls of sheath 100 and elongate member 160. This clearance can also be described as an annular space. Furthermore, the second profile can also comprise a predetermined maximum, such as a maximum diameter, i.e., inverted sheath 100 will not expand or inflate beyond a predetermined second profile within a predetermined pressure threshold. However, as will be described in further detail below, inverted sheath 100 comprising a balloon can further comprise a third profile. The transition to a third profile can be achieved by inflating the balloon.

In some embodiments, eversion motion can be actuated or facilitated by a fluid 120. Inverted sheath 100 can be configured to receive a fluid 120 and obtain a sufficient fluid pressure to trigger sufficient eversion of inverted portion 101. For example, inverted sheath 100 transitions to the second profile by receiving and sufficiently retaining fluid 120 between walls of sheath 100. In this pressurized state, inverted sheath 100 comprises a chamber 130 defined by walls 104 and 105 of the inverted portion 101, neck portion 102, and optionally, elongate member 160. Pressurization of inverted sheath 100 can produce a sufficient clearance between walls 104 and 105 to reduce or substantially eliminate friction and in some embodiments, can cause foreshortening and/or axial displacement of inverted sheath 100. In an embodiment, pressures for facilitation of eversion can be approximately 2-4 atmospheres; however, a person of ordinary skill will appreciate that the requisite pressure to evert inverted sheath 100 may vary.

An inverted sheath 100, in accordance with the present disclosure, comprises a tubular form turned inward upon itself, either partially or completely, to form overlapping layers. Overlapping layers comprise at least one inner layer 104 and an outer layer 105; however, inverted sheath 100 can comprise more than two overlapping layers. In other embodiments, inverted sheath 100 can comprise a tubular form layered over another tubular form wherein at least one set of proximate ends are connected to each other.

Tubular form comprises any elongated structure with a lumen extending through from a proximal to distal end. Accordingly, tubular form need not have a circular cross-section, but rather could be oval, elliptical, any polygonal shape, or randomly shaped. The tubular form can comprise a uniform or varying cross-section along its length. The tubular form can comprise a straight, curved, or bent longitudinal axis.

In an embodiment, inverted sheath 100 comprises a first end 107 and a second end 108. First end 107 can be folded inward to create at least one inner layer 104, an outer layer 105, and a fold 106. Fold 106 can be located at a proximal or distal end of inverted sheath 100. In an embodiment configured to evert in a distal to proximal direction, first end 107 is fixedly connected to elongate member 160 proximal medical device 150. Optionally, second end 108 can be slidably or fixedly connected to elongate member 160 or a retracting member 180, if present, proximal to the site at which first end 107 is connected. If everting in a proximal to distal direction, the above-described configuration can be reversed. Furthermore, in an embodiment configured to evert hydraulically, the connection can be sufficiently leak-proof to allow the requisite pressure to be achieved inside chamber 130 so that inverted sheath 100 is retracted.

Optionally, a tubular form can be configured to resist expanding or inflating beyond a predetermined second profile, as previously described. For example, the tubular form can comprise a minimally elastic material or a reinforcement member. In an embodiment, inverted sheath 100 can comprise a tubular form and a biased, helically wound or braided member. This member can be over or under-laid, embedded, or otherwise associated with a tubular form. This member can comprise an elongated thread, fiber, film, or tape, e.g., tape comprising ePTFE.

In various embodiments, inverted sheath 100 can be in fluid communication with a fluid conduit 135. Fluid conduit 135 comprises any structure configured to transport fluid 120 to chamber 130. For example, elongate member 160 can comprise a lumen which serves as fluid conduit 135. In other embodiments, neck portion 102 can comprise fluid conduit 135. For example, neck portion 102 can extend along a substantial length of elongate member 160 and fluid 120 can be transported in the luminal space between neck portion 102 and elongate member 160.

In various embodiments, fluid conduit 135 can be in fluid communication with chamber 130 via a fluid port 140. Fluid port 140 comprises an access point for fluid 120 to enter into chamber 130. In an embodiment, a fluid port 140 is locatable within the wall of elongate member 160 such that fluid 120 travels in a proximal to distal direction through a lumen and exits radially through fluid port 140. In other embodiments, fluid port 140 is locatable within the wall or at an end 107, 108 of inverted sheath 100.

Fluid 120 can comprise a liquid, gas, gel, or combination thereof. In an embodiment, fluid 120 is biocompatible, such as saline solution. Fluid 120 can also comprise a contrast agent. Using a contrast agent to facilitate hydraulic deployment allows a clinician to monitor and evaluate delivery and deployment of a medical device.

In an embodiment, an inverted sheath 100 can be configured to be "neckable" or capable of "necking down." Neckability describes the ability of a material or structure to elongate and reduce in cross-sectional area when placed under tension. In an embodiment, inverted sheath 100 comprises a tubular form configured to narrow in diameter and elongate when in tension. For example, tubular form can comprise a braided filament or biased, helically wound tape which is fitted, embedded or otherwise encased with tubular form. In addition, inverted sheath 100 can comprise more than one layer of biased, helically wrapped or braided tubular forms surrounding medical device 150 to increase the compression force and the extent to which medical device 150 can be compressed. In addition, sheath 100 can comprise biased, helically wrapped or braided tubular forms in which the angle of wrap or braid, relative to the tubular (longitudinal) axis is varied to result in different rates and forms of eversion.

In an embodiment, inverted sheath 100 can comprise the ability to foreshorten. For example, inverted sheath 100 comprising a tubular form and elements such as braided filaments or biased, helically-wrapped film tapes comprise the ability to foreshorten. In an embodiment, a tubular form comprising the ability to foreshorten has the elements lying at an angle (relative to a tubular axis) of less than the "neutral angle." The neutral angle (sometimes also referred to as the "Magic Angle"), in a cylindrical vessel under internal, isostatic pressure, is theoretically 54.7°, but varies there from in the present embodiment depending on externally-applied forces and the materials used. In general, the neutral angle is the angle at which braided and/or wrapped tensile elements satisfy equilibrium under internal isostatic pressure provided the influence of the matrix material is neglected.

In various embodiments, sheath 100 features the following characteristics. Sheath 100 has a diameter prior to loading over medical device 150 larger than the profile (diameter) of the compressed device 150. Sheath 100 can then be simultaneously and/or subsequently necked down over device 150, reducing the profile of sheath 100, and thereby reducing the difference between the profile of the sheath 100 and the profile of compressed medical device 150 and thus reducing the delivery profile. At the time of deployment, as diameter increases, the angle of the elements approaches the neutral angle. Sheath 100 can foreshorten upon the change from the necked angle, $\phi_1$, to the neutral angle, $\phi_2$, at pressurization.

In some embodiments, a tubular member, used to construct inverted sheath 100, can be made as follows. A film tape is biased and helically wrapped about a mandrel, i.e., a wrap in one direction at a given angle is followed by at least one wrap in the opposite direction over the previously wrapped material, typically at an equal but opposite angle. The diameter of the mandrel and hence the diameter of the wrapped tube is desirously greater than that of the compressed medical device (to allow loading and subsequent necking to further constrain the device) but is more closely determined in accordance with the formula listed below, to be referred to in conjunction with FIGS. 1A and 1B, and the schematics shown in FIGS. 8A and 8B. Similarly, the required diameter of the sheath 100 when the elements reach the neutral angle can also be determined using the following formula:

$$d_2 = d_1 \sin \theta_2 / \sin \theta_1.$$

Figure 8A:
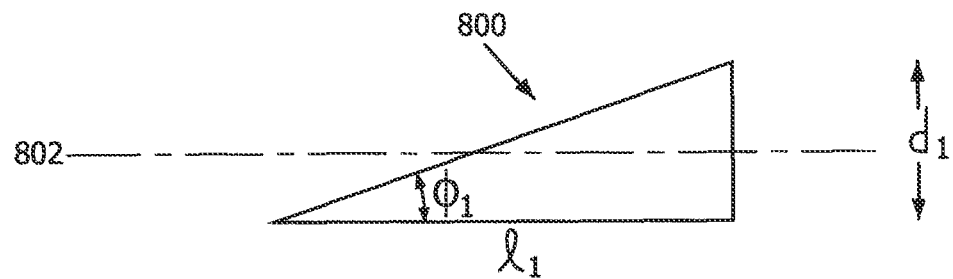
FIGS. 8A and 8B are schematics illustrating certain dimensional relationships of the present disclosure.
Figure 8B:
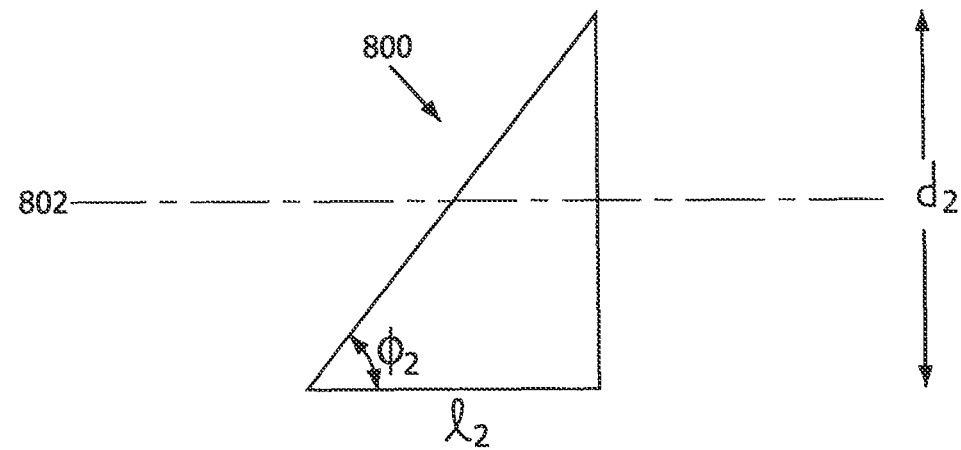

Referring to the schematic in FIG. 8A and FIGS. 1A and 1B, a portion of a helically oriented wrapped element (800) is shown relative to the tubular axis 802. These multiple elements (when wound) comprise the tubular member used to construct sheath 100. The elements can under- or over-lay other elements wrapped in a biased fashion. Element 800, has an angle $\theta_1$ as loaded over a medical device (the "loaded angle"). The tubular member, as loaded over the device, has a length $l_1$, and diameter $d_1$ (the "loaded diameter"). Referring to FIG. 8B, the element is shown at the point the neutral angle ($\theta_2$) is achieved and shows the change in loaded diameter from $d_1$ to $d_2$ and loaded length from $l_1$ to $l_2$. It is important to note that in both FIGS. 8A and 8B, the hypotenuse length of the element, i.e., the length along the strength orientation, does not change between the two states.

In operation, pressurization of sheath 100 causes a change in angle from $\theta_1$ to $\theta_2$ and a resulting change in diameter of the sheath 100 from $d_1$ to $d_2$. The desire is to at least approach the neutral angle ($\theta_2$) upon pressurization of the inverted sheath 100 in order to create a separation (and minimize friction) between layers 104 and 105, as well as generate eversion by foreshortening of sheath 100. Upon application of pressure, which changes the angle and increases the space between sheath layers 104, 105 in everting portion 101 and/or sheath layer 105 in neck portion 102 and elongate member 160, sheath 100 foreshortens. Simultaneously, this foreshortening begins to evert sheath 100 off of the medical device. As the angle θ changes and approaches the neutral angle, further foreshortening occurs along sheath 100 in everting portion 101 and/or neck portion 102. Thus, by using the formula above one can determine the desired diameter at the neutral angle, the loaded angle ($\theta_1$), loaded diameter ($d_1$) and even the change in length from $l_1$ to $l_2$ can be determined and used to construct a sheath 100 appropriate for use with a given medical device having certain compressed and delivered diameters. Upon pressurization of chamber 130 and resultant separation of layers 104 and 105 and change in angle from loaded angle toward neutral angle, inverted sheath 100 expands in a radial direction and contracts in a longitudinal direction. That is, the braid or winding angle tends to return to the neutral angle when an internal pressure is applied, and as a result, inverted sheath 100 shortens in length, i.e. foreshortens.

Sheath 100 can comprise any material or materials which, when configured as an evertable tube, facilitate a low turn radius at fold 106, which is the diametric transition zone as sheath 100 everts. In various embodiments, sheath 100 further comprises a material that has the ability to decrease in diameter upon elongation and shorten in length upon an increase in diameter. Sheath 100 can be comprised of a wide range of materials such as polyamides (e.g., nylons), polycarbonates, polyethylenes, polypropylenes, fluoropolymers (e.g., PTFE and ePTFE), polyvinyl chlorides, polyurethanes, elastomers (e.g., polysiloxanes), and other biocompatible materials. Different portions of sheath 100 can comprise different or the same materials.

In an embodiment, sheath 100 is constructed of anisotropic material(s), i.e., materials having a physical property (such as tensile strength) that has a different value when measured in different directions. Sheath 100 can be constructed of an anisotropic material such as an ePTFE film tape which exhibits a higher strength in the "machine direction" as opposed to that in the transverse direction. In an embodiment, sheath 100 is constructed of anisotropic film tapes with their highest strength in the length dimension which are wound into a tubular form at angles analogous to a filament braid or weave. In other words, the film tapes are strength oriented in the direction of the wrap. Sheath 100 can also comprise a braided filament tube or bias-wrapped tube construction as long as a force (e.g., pressure, can be applied and contained within the sheath. Sheath 100 preferably exhibits the ability to vary in length and diameter in response to the application of pressure.

Anisotropic materials can, in certain cases, be preferred because their strength orientation along the wrap or braid direction defines relative angles which allow predictions of the relationship between diameter and length. Anisotropic tube constructs can allow necking without straining their tensile members. On the other hand, materials which have no specific strength orientation (i.e. isotropic) strain in all directions resulting in a less direct relationship between diameter and length changes. This disadvantage is further compounded by the fact isotropic materials can be permanently deformed during the application of force.

In some embodiments, sheath 100 can optionally comprise a temporal or releasable anchor at or near the distal tip fold 106 to prevent premature foreshortening and/or eversion of inverted sheath 100. A distal tip anchor can comprise a releasable restraining member, or a releasable adhesive, at or near fold 106. For example, with reference to FIG. 1C, restraining member may comprise a flexible band or o-ring 108 that is fitted on the distal end, e.g., in between the inner and outer layer of inverted sheath proximate to fold.

Restraining member 108 can roll in a proximal direction as inverted sheath everts, once the axial force overcomes the rolling friction of the restraining member. In other embodiments, restraining member can comprise a corrugated surface on the elongate member 160 or the like which improves stabilization. Similarly, distal tip fold 106 can be anchored through the application of a soft polymer adhesive material, a gel, a wax material, or some other type of tacky or otherwise securing substance (collectively "adhesive agent") to the interior wall of the inner layer 104 and/or to the distal region of elongate member 160 to prevent premature eversion. The soft polymer adhesive material will release from distal region of elongate member 160 and inverted sheath 100 will evert once the axial force overcomes the adhesion force. Examples of soft polymer adhesives include, inter alia, a thermoplastic copolymer of tetrafluoroethylene and perfluoroalkylvinylether as described in U.S. Pat. No. 8,048,440 to Chang et al., and acrylate based polymers.

Similarly, to prevent premature eversion, adhesive agent can be placed in between inner layer 104 and outer layer 105. The adhesive agent can be released by the introduction of fluid 120. The pressure from fluid 120 can separate layers 104 and 105, or the fluid can actually hydrate the adhesive agent, causing a loss in its binding/adhesive properties. In further embodiments, the adhesive agent, upon mixing with fluid 120, can actually increase the lubriciousness of fluid 120. In an embodiment, a hydrogel coating, such as poly vinyl alcohol, can be applied in between layers 104 and 105, and upon drying, secures layers 104 and 105 together. Upon introduction of an aqueous fluid, the hydrogel is hydrated which releases layers 104 and 105 and increases the lubriciousness of fluid 120.

In an embodiment, inverted sheath 100 can further comprise a radiopaque marker to facilitate delivery and deployment. For example, fold 106 can comprise a radiopaque marker to indicate a location of the device and/or pre- and post-everted state. A radiopaque marker can comprise one or more of tungsten, gold, platinum and the like. Fold 106 can also be elastomeric to facilitate loading of medical device 150 onto elongate member 160.

Referring to FIG. 1D, in a further embodiment, inverted sheath 100 can comprise a retracting member 180. Retracting member 180 comprises any structure configured to aid in eversion of inverted sheath 100. For example, retracting member 100 can comprise a coaxial tube, a tether, or a wire connected to inverted sheath 100 in order to transfer an axial retraction force to inverted sheath 100. Retracting member 180 comprises any biocompatible material. In an embodiment, retracting member 180 can comprise a polymeric or metallic material.

Retracting member 180 can be retracted by axial displacement. By way of example, axial displacement can occur by manually pulling a proximal end of retracting member 180, or in other embodiments, as depicted in FIG. 1D, by winding retracting member 180 onto a retraction wheel 185. Retraction wheel 185 can be any revolving structure located at a proximal end around which retracting member 180 can be wound.

Retracting member 180, as mentioned previously, can optionally comprise a coaxial tubular member which circumscribes neck portion 102 of inverted sheath 100. In an embodiment, the tubular member can comprise a structurally weak section 181 such that tubular retracting member can tear down its length to facilitate reeling in with the use of a retraction wheel. The weak section 181 can comprise a small cut to initiate a tear path, a perforated line, and/or a lower density or thinned section along the length. This illustrated embodiment depicts an inverted sheath comprising neck portion 102 that extends along a substantial length of elongate member 160, and as the retracting member 180 is spooled onto retraction wheel 185, neck portion 102 can gather at the proximal region 161 of elongate member 160.

Fluid can be introduced into chamber and reduce friction between layers of inverted portion 101 to aid in retraction. Fluid can also be introduced to cause foreshortening. Foreshortening can completely or partially uncover medical device 150.

In various embodiments, again with reference to FIG. 1D, to aid in retraction, a constraining sheath delivery system can optionally comprise a coaxial housing 187 that extends along proximal portion of elongate member 160. During retraction, coaxial housing 187 is dimensioned so that it can contain, compact, or re-neck sheath 100, e.g., after it has been altered to a neutral angle or otherwise increased diameter/width. In an embodiment, housing 187 comprises an elongated tubular member which can have same or similar properties as elongate member 160 with respect to flexibility.

In addition, coaxial housing 187 in combination with fixing the volume of chamber 130 (once fluid 120 has been introduced) can enhance sheath 100 eversion by partially maintaining an increased pressure within chamber 130 during foreshortening. The volume of chamber 130 can become fixed by locking the inflation port. Coaxial housing 187 can be dimensioned to constrict sheath 100. As a result, once fluid is introduced and eversion begins, a larger portion of fluid 120 remains about inverted portion 101 than it otherwise would in an ever decreasing volume within chamber 130. Higher pressures help maintain the angle of the wrap or braid at $\theta_2$ or minimize deviation there from.

Embodiments comprising a wrapped sheath generally pertain to a neck portion 102 comprising the same wrap angle as inverted portion 101. However, it is also contemplated that neck portion 102 can comprise a different wrap angle than inverted portion 101, specifically, neck portion 102 can comprise a wrap angle of $\theta_2$ and inverted portion 101 can comprise a wrap angle of $\theta_1$. Upon fixing the volume within chamber 130, tension can be applied across neck portion 102 to reduce its profile or diameter, and thereby increasing volume of fluid 120 into inverted portion 101. Coaxial housing 187 can constrict sheath 100 about inverted portion 101 to minimize the tendency for the pressure to equalize.

In an embodiment, inverted sheath 100, in a first profile, can comprise a torqued, twisted or asymmetric wrap or braid configuration to rotate a medical device upon pressurization as inverted sheath 100 is deployed.

With reference now to FIGS. 2A-2B, inverted sheath 200 can be axially displaced by rolling along elongate member 260 in response to chamber 230 pressurization with fluid 220. For example, inverted sheath 200 is configured to have unequal cross-sectional areas at opposite ends of inverted sheath 200 upon fluid pressurization such that inverted sheath 200 will roll along elongate member 260 in the direction of the end with greater cross sectional area. FIG. 2C depicts a cross-sectional area (shaded region) of inverted portion 201. FIG. 2D depicts a cross-sectional area (shaded region) of a neck portion 202. In comparison, neck portion 202 has a greater cross-sectional area than inverted portion 201. This difference in cross-sectional area causes inverted portion 201 to evert as it rolls along elongate member 260.

Figure 3:
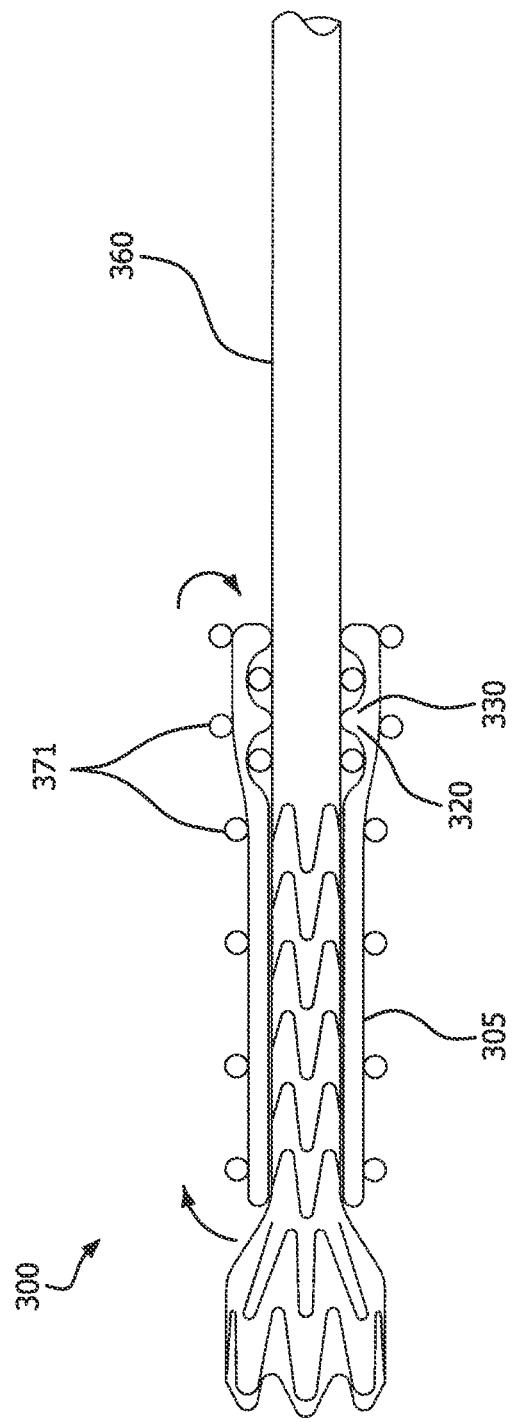
FIG. 3 illustrates a cross-sectional view of an evertable sheath embodiment in a rolling configuration constraining a medical device loaded onto an elongate member.

With reference to FIG. 3, a further embodiment can comprise inverted sheath 300 having at least one ring 371 to enhance foreshortening of sheath 300. Ring 371 is configured to be initially positioned on the exterior of sheath 300 and upon eversion to be repositioned between sheath 300 and the surface of elongate member 360. In doing so, ring 371 works to take up the length of sheath 300 over a shorter length of elongate member 360. Ring 371 can also be configured to be inflatable. Ring 371 can also be made of an elastomeric material. In an alternative embodiment, the surface of elongate member 360 can be corrugated in the region onto which sheath 300 everts.

Figure 4A:
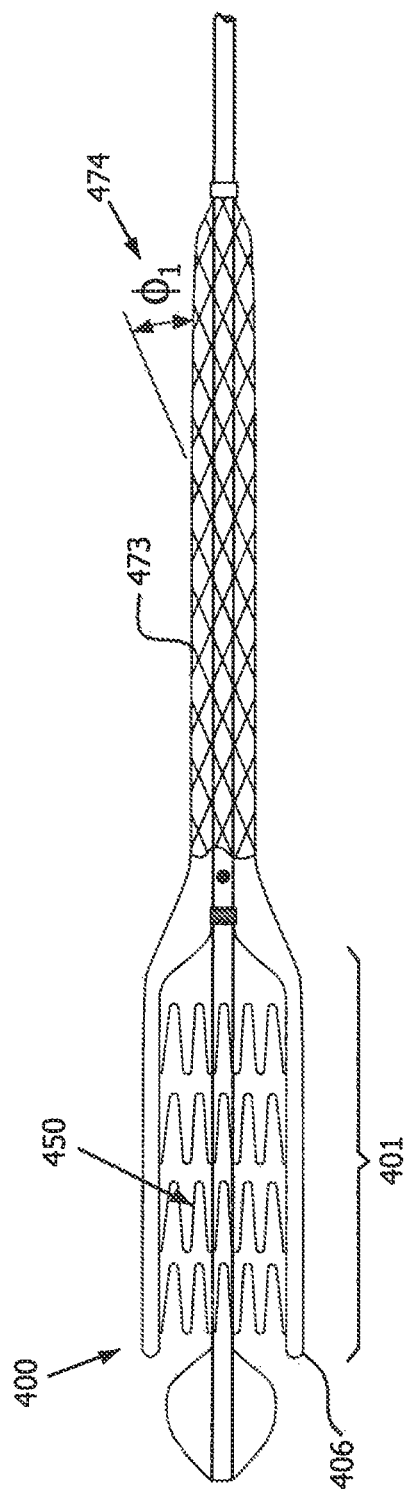
FIGS. 4A-4B illustrate a cross-sectional view of an evertable sheath embodiment in a foreshortening configuration constraining a medical device loaded onto an elongate member.
Figure 4B:
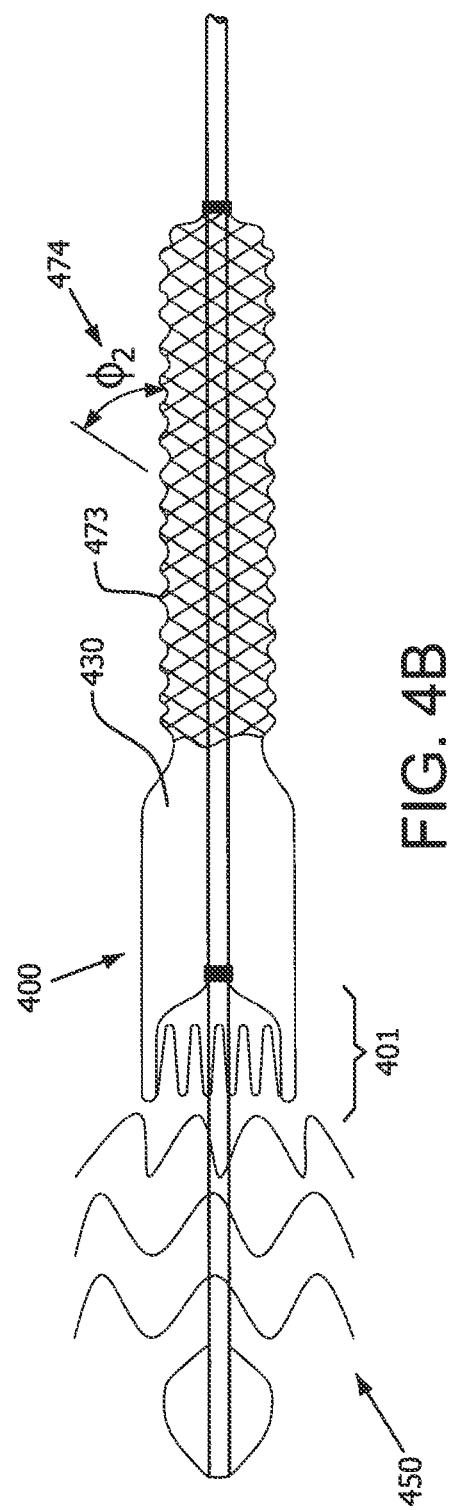

With reference now to FIGS. 4A-4B, inverted sheath 400 can be configured to foreshorten in response to chamber 430 pressurization, i.e. as inverted sheath 400 expands in diameter it shortens in length. The change in length is equal to the amount of sheath 400 eversion from medical device 450, because the end opposite fold 406 can be fixedly connected, i.e., resistant to shortening.

In an embodiment, inverted sheath 400 comprises a tubular form with a braided or helically-wrapped filament member 473 over- or under-laid on at least a portion of sheath 400 or otherwise incorporated into sheath 400. Prior to pressurization, the filaments 473 lay at an angle 474 less than the neutral angle. This neutral angle is theoretically 54.7°, but varies there from depending on externally-applied forces and the materials used. Upon pressurization of chamber 430, inverted sheath 400 expands in a radial direction and, due to contact with filament member 473, foreshortens in a longitudinal direction; that is, the braid or winding angle 474 tends to return to the neutral angle when an internal pressure is applied, and as a result, the inverted sheath shortens in length.

In addition, the amount of foreshortening of inverted sheath 400 under pressurization depends on the initial braid or winding angle 474 of a filament member 473, such as a tape. The initial braid or winding angle 474 can be varied to achieve a desired amount of eversion. Similarly, the length of inverted sheath 400 can be varied to achieve a desired diameter and length change, and resulting eversion when pressurized.

Figure 5A:
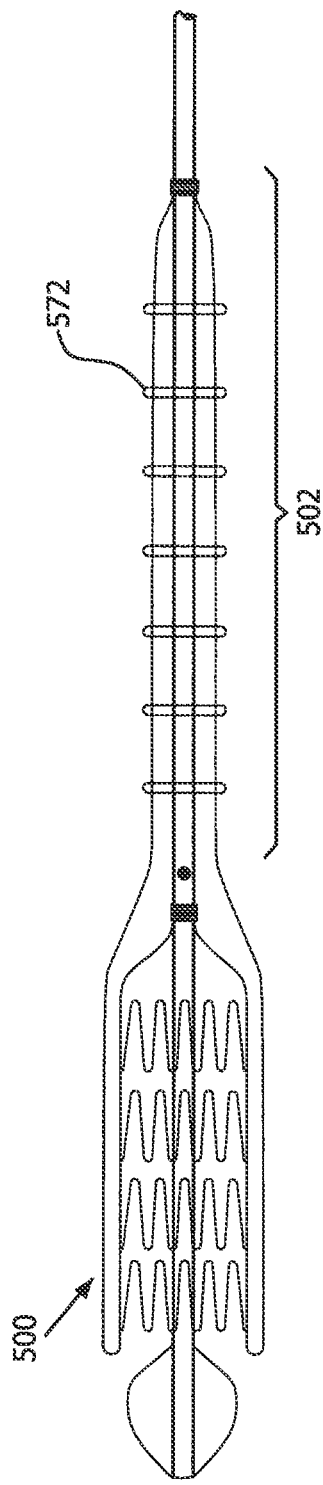
FIGS. 5A-5B illustrate a cross-sectional view of an exemplary evertable sheath in a foreshortening configuration constraining a medical device loaded onto an elongate member.
Figure 5B:
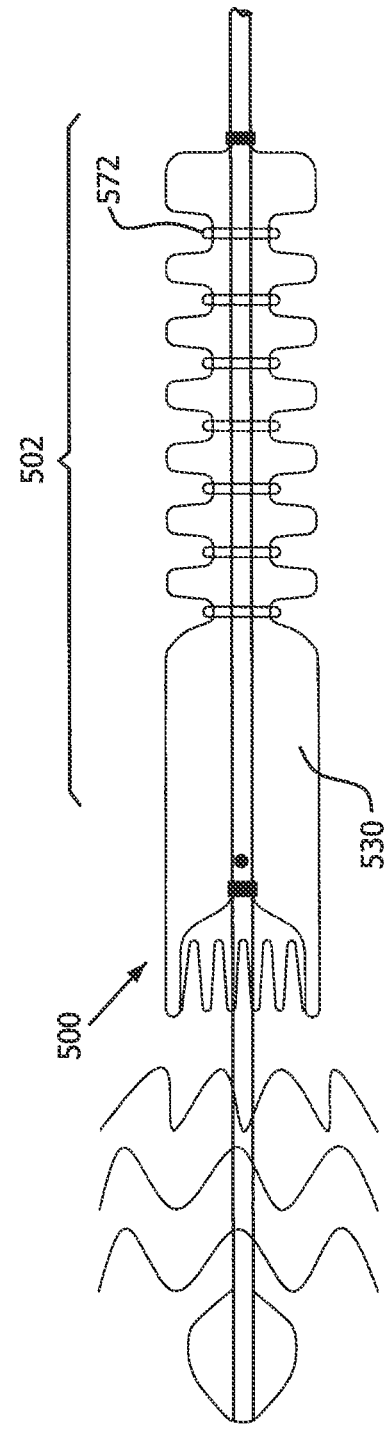

With reference now to FIGS. 5A-5B, another foreshortening configuration can comprise inverted sheath 500 comprising at least one constriction 572 locatable in neck portion 502. Constriction 572 comprises any structure configured to maintain a substantially constant diameter of chamber 530 at the site applied during pressurization. For example, constriction 572 can comprise a physical restraint, such as a clamp, suture, or weld, or a chemical restraint, such as an adhesive. Inverted sheath 500 comprising constriction 572 is configured to foreshorten upon chamber 530 pressurization. In an embodiment, inverted sheath 500 comprises more than one constriction 572. In other embodiments 500 comprises a helically wrapped constriction 572. The number of constrictions 572 and neck 502 length can be varied to achieve a desired amount of eversion.

Figure 6A:
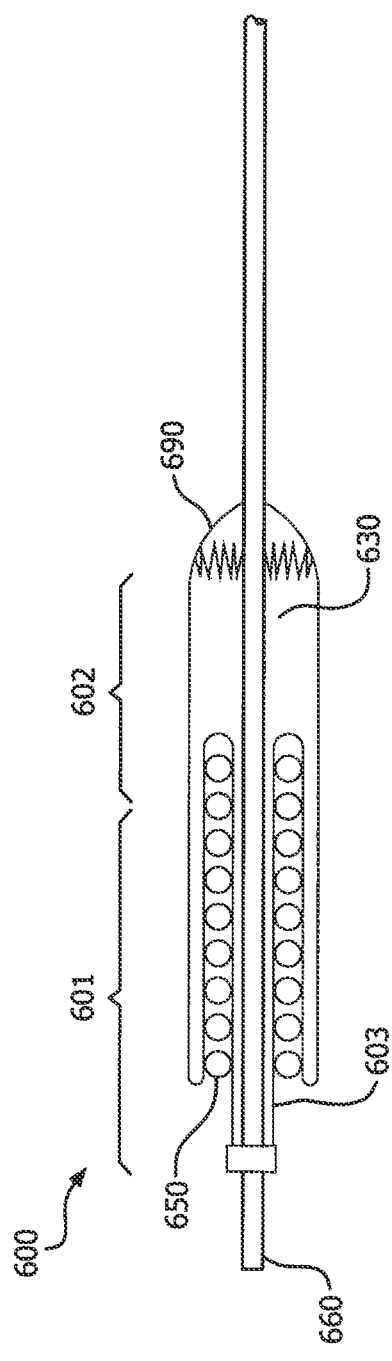
FIGS. 6A-6B illustrate a cross-section of an exemplary evertable sheath comprising a balloon portion.
Figure 6B:
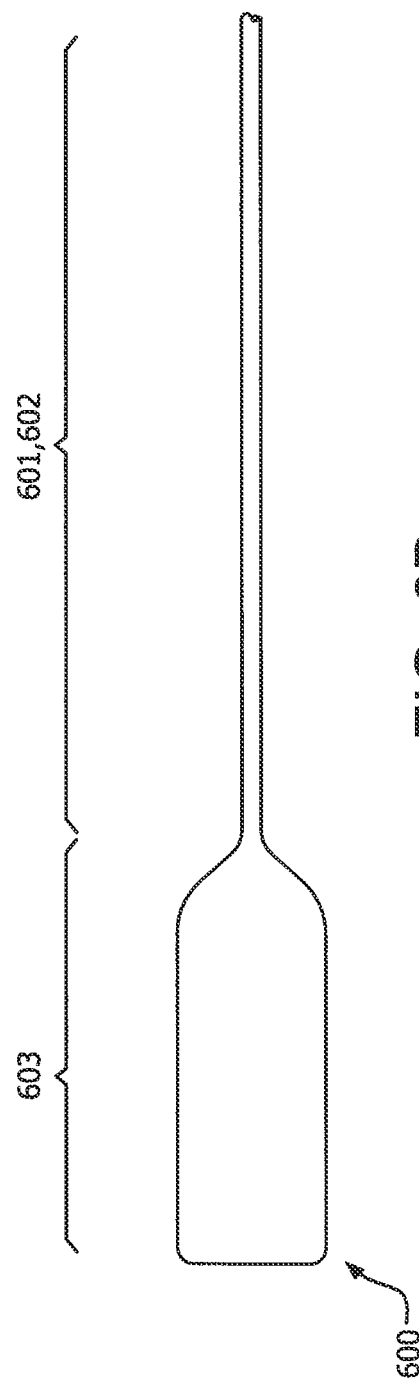

With reference now to FIGS. 6A-6C, inverted sheath 600 can comprise an inverted portion 601, neck portion 602, and a balloon portion 603. Balloon 603 comprises a portion of inverted sheath 600 that medical device 650 circumscribes. Balloon 603 can be configured to inflate concurrently with or subsequent to eversion of inverted portion 601. For example, balloon 603 can be in fluid communication with chamber 630. In the case of a balloon inflating concurrently, balloon 603 can be configured to inflate at the same pressure required for eversion. In the case of a balloon inflating subsequently, balloon 603 can be configured to inflate at a second pressure, wherein eversion occurs at a lower first pressure. Balloon 603 can be configured to expand medical device 650, or to positionally or structurally adjust an already expanded medical device 650.

Balloon 603 can be integral with constraining sheath 600, or alternatively, balloon 603 can be manufactured separately and assembled together. In an embodiment, balloon 603 and inverted portion 601 and neck portion 602 can be wrapped integrally on a stepped mandrel, and before inverting constraining sheath 600, would look similar to FIG. 6B or FIG. 6C(1).

Balloon 603 formation can also be carried out in any conventional manner using known extrusion, injection molding and other molding techniques. Typically, there are three major steps in the process that include extruding a tubular pre-form, molding balloon 603 and annealing balloon 603. Depending on the method of manufacturing balloon 603, the pre-form can be axially stretched before it is blown. Techniques for balloon 603 formation are described in U.S. Pat. No. 4,490,421 to Levy; RE32,983 to Levy; RE33,561 to Levy; and U.S. Pat. No. 5,348,538 to Wang et al., all of which are hereby incorporated by reference. Balloon 603 can also be tape wrapped. Balloon 602 can be made in the same or similar manner as inverted portion 601 and/or neck portion 602. Balloon 603 can then be coupled to inverted portion 601.

Balloon 603 can be formed from using any materials known to those of skill in the art. Commonly employed materials include the thermoplastic elastomeric and non-elastomeric polymers and the thermosets including the moisture curable polymers. Examples of suitable materials include but are not limited to, polyolefins, polyesters, polyurethanes, polyamides, polyimides, polycarbonates, polyphenylene sulfides, polyphenylene oxides, polyethers, silicones, polycarbonates, styrenic polymers, copolymers thereof, and mixtures thereof. Some of these classes are available both as thermosets and as thermoplastic polymers. See U.S. Pat. No. 5,500,181 to Wang et al., for example, which is hereby incorporated by reference. As used herein, the term "copolymer" shall be used to refer to any polymer formed from two or more monomers, e.g., 2, 3, 4, 5, etc.

Useful polyamides include, but are not limited to, nylon 12, nylon 11, nylon 9, nylon 6/9 and nylon 6/6. The use of such materials is described in U.S. Pat. No. 4,906,244 to Pinchuk et al., for example, which is hereby incorporated by reference.

Examples of some copolymers of such materials include the polyether-block-amides, available from Elf Atochem North America in Philadelphia, Pa. under the trade name of PEBAX®. Another suitable copolymer is a polyetheresteramide.

Suitable polyester copolymers include, for example, polyethylene terephthalate and polybutylene terephthalate, polyester ethers and polyester elastomer copolymers such as those available from DuPont in Wilmington, Del. under the trade name of HYTREL®.

Block copolymer elastomers such as those copolymers having styrene end blocks, and midblocks formed from butadiene, isoprene, ethylene/butylene, ethylene/propene, and so forth can be employed herein. Other styrenic block copolymers include acrylonitrile-styrene and acrylonitrile-butadiene-styrene block copolymers. Also, block copolymer thermoplastic elastomers in which the block copolymer is made up of hard segments of a polyester or polyamide and soft segments of polyether can be employed herein.

Specific examples of polyester/polyether block copolymers are poly(butylene terephthalate)-block-poly(tetramethylene oxide) polymers such as ARNITEL® EM 740, available from DSM Engineering Plastics and HYTREL® polymers available from DuPont de Nemours & Co, already mentioned above.

Suitable materials that can be employed in balloon 603 formation are further described in, for example, U.S. Pat. No. 6,406,457 to Wang et al.; U.S. Pat. No. 6,284,333 to Wang et al.; U.S. Pat. No. 6,171,278 to Wang et al.; U.S. Pat. No. 6,146,356 to Wang et al.; U.S. Pat. No. 5,951,941 to Wang et al.; U.S. Pat. No. 5,830,182 to Wang et al.; U.S. Pat. No. 5,556,383 to Wang et al.; U.S. Pat. No. 5,447,497 to Sogard et al.; U.S. Pat. No. 5,403,340 to Wang et al.; U.S. Pat. No. 5,348,538 to Wang et al.; and U.S. Pat. No. 5,330,428 to Wang et al., all of which are hereby incorporated by reference.

The above materials are intended for illustrative purposes only, and not as a limitation on the scope of the present disclosure. Suitable polymeric materials available for use are vast and too numerous to be listed herein and are known to those of ordinary skill in the art.

Referring to FIGS. 6C(1) to 6C(4), balloon portion 603 of inverted sheath 600 can be conventionally folded down (as commonly known in the art), to a configuration as shown in FIG. 6C(2). Alternately, balloon portion 603 may be configured to radially distend upon the application of internal pressure, and therefore could be applied to the elongate member 660 in a small state and eliminate the need of the folding step. In either case, medical device 650 is then diametrically reduced to a profile conducive to use in endovascular applications, as shown in FIG. 6C(3). While in this reduced diametrical state, inverted portion 601 of inverted sheath 600 is placed upon medical device 650. Neck portion 602 of inverted sheath 600 may then be affixed to elongate member 660.

As shown in FIG. 6A, one end of sheath 600 can optionally attach to an olive 690 which is axially slidable along elongate member 660. Olive 690 can be configured to slidably seal around elongate member 660. In a further embodiment, elongate member 660 can comprise a barrier past which olive 690 can not extend. This can serve as an indicator to clinicians that eversion is complete. Barrier can also comprise a radio-opaque material to further facilitate this function.

In other embodiments, an elongate member can comprise a balloon, as an alternative to being incorporated into an inverted sheath, wherein the balloon can also be in fluid communication with the same fluid conduit as inverted sheath. Similar to above, the balloon can be configured to inflate concurrently with or subsequent to eversion.

A device delivery system and balloon combination is advantageous in that no further endovascular tool exchanges are needed to facilitate balloon "touch-up" of the implanted medical device. Fewer exchanges reduce peri-procedural time resulting in better patient outcomes and overall reduction in radiation exposure for both patient and clinical staff.

Figure 7:
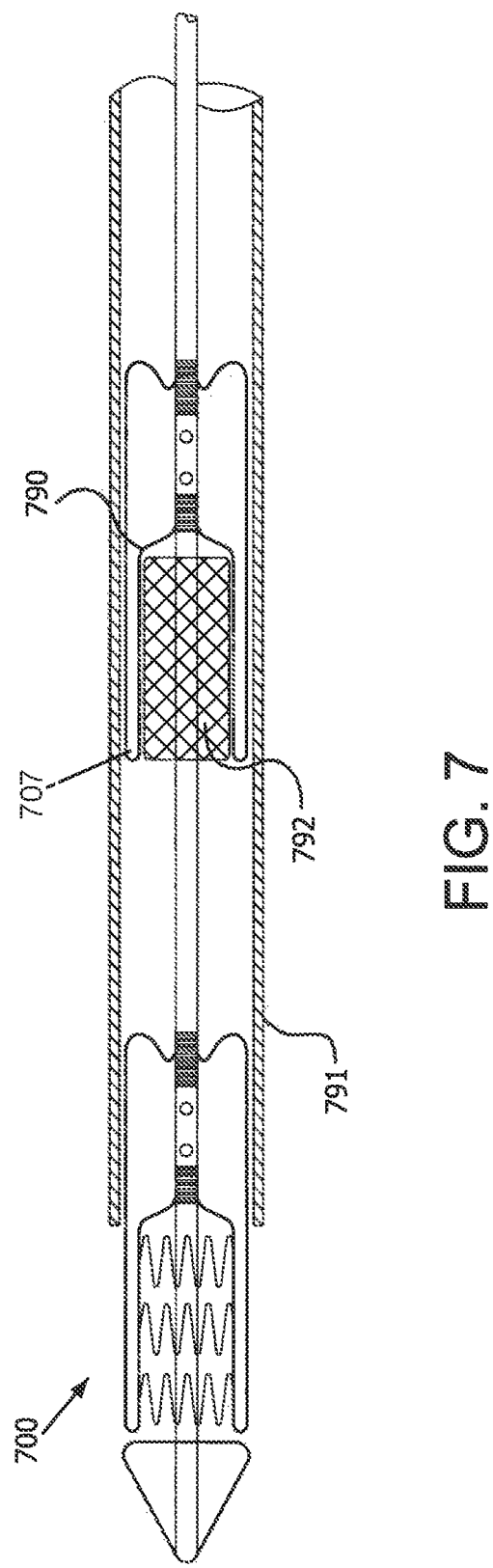
FIG. 7 illustrates a cross-section of an eversion system comprising an evertable sheath and a supplemental sheath.

With reference now to FIG. 7, a deployment system can comprise an inverted sheath 700 and a supplemental sheath 790 arranged to amplify axial force and thereby facilitate eversion. For example, deployment system can comprise an inverted sheath 700 connected to at least one supplemental sheath 790. Supplemental sheath 790 can comprise inverted sheath, as described herein, but a foreshortening sheath need not be inverted. Instead, first end 707 can be connected to or frictionally engaged with inverted sheath 700.

The inverted sheath 700 and a supplemental sheath 790 can be connected by a linkage 791. As such, linkage 791 comprises any device that is frictionally engaged or fixedly connected to inverted sheath 700 and supplemental sheath 790 such that motion of supplemental sheath 790 is translated to inverted sheath 700. For example, linkage 791 can comprise a coaxial tube that frictionally fitted to sheaths 700,790 upon pressurization.

When supplemental sheath 790 comprises a rolling configuration, bridge 792 can provide the differential for the cross-sectional area in lieu of medical device. Bridge 792 can comprise a collapsed configuration and an expanded configuration. Bridge 792 can also be self-expanding.

Similarly, in other embodiments, a deployment system can comprise more than one inverted sheath mounted along elongate member to deploy one or more medical devices. Alternatively, a deployment system can comprise inverted sheath configured to deploy one or more medical devices.

In another embodiment, a deployment system can comprise an inverted sheath as described herein, and a sleeve wherein the sleeve is attached proximal the distal end of the inverted sheath and configured to be a mechanism for retracting the sleeve. In this embodiment, the inverted sheath may or may not be constraining a medical device. Furthermore, the sleeve can be configured to at least partially constrain a medical device.

Similar to the sheath as described herein, a sleeve can be comprised of a wide range of materials such as polyamides (e.g., nylons), polycarbonates, polyethylenes, polypropylenes, fluoropolymers (e.g., PTFE and ePTFE), polyvinyl chlorides, polyurethanes, elastomers (e.g., polysiloxanes), and other biocompatible materials. Sleeve can comprise any material or materials which has the ability to decrease in diameter upon elongation and shorten in length upon an increase in diameter. In an embodiment, a sleeve is constructed of anisotropic material(s), i.e., materials having a physical property (such as tensile strength) that has a different value when measured in different directions. A sleeve can be constructed of an anisotropic material such as an ePTFE film tape which exhibits a higher strength in the "machine direction" as opposed to that in the transverse direction. In an embodiment, a sleeve is constructed of anisotropic film tapes with their highest strength in the length dimension which are wound into a tubular form at angles analogous to a filament braid or weave. A sleeve can also comprise a braided filament tube or bias-wrapped tube construction so long as an externally-applied force (e.g., pressure) can be applied.

In accordance with the present disclosure, a method of loading a medical device can comprise the steps of radially compressing a medical device, as described herein, onto the distal end of an elongate flexible catheter having proximal and distal ends; covering the medical device and the catheter with an inverted sheath as described herein; and applying tension to the sheath in order to neck down the medical device to the catheter such that the sheath obtains a first profile or substantially conforms to the shape of the medical device.

Similarly, a method of loading a medical device can comprise placing a medical device in the interior of a tubular form, wherein the tubular form can be an uninverted form of an inverted sheath; inverting the tubular form to form two layers over the medical device. In an embodiment, the medical device can be constrained within the sleeve on the distal region of an elongate member or just beyond the distal end of the elongate member. During deployment, the device would be back loaded on a guide wire and traverse the guide wire to the delivery site. By constraining medical device at a location just beyond the distal end of the catheter, further reductions in profile can be realized.

In accordance with the present disclosure, a method of deploying a medical device can comprise the steps of positioning an inverted sheath and a medical device, as described herein, at a desired location; introducing a fluid to form a chamber as described herein, wherein when the inverted sheath receives the fluid, the inverted sheath expands into a second profile and everts, thereby uncovering the medical device. A further step can comprise inflating a balloon. The balloon can be used to facilitate contact with a surrounding tissue. Likewise, the balloon can expand in order to expand or to positionally or structurally adjust the medical device. Balloons treated with delicate or flaky or crystalline therapeutic agents and/or any coating that can particulate, benefit greatly from an everting, non-sliding sheath that protects against inadvertent drug loss during delivery to the therapy site and deployment.

It will be apparent to those skilled in the art that various modifications and variations can be made in the present disclosure without departing from the spirit or scope of the disclosure. Thus, it is intended that the present disclosure cover the modifications and variations of this disclosure provided they come within the scope of the appended claims and their equivalents.

What is claimed is:

1. A method of delivering a medical device comprising:
positioning a radially compressed medical device within a vessel, the medical device being covered by a sheath having a delivery profile wherein the sheath is inverted to define an inner layer and an outer layer, wherein a pressurizable chamber is defined between the inner and outer layers, and the sheath defines a maximum outer diameter; and
pressuring the pressurizable chamber to cause the sheath to transition from the delivery profile to a deployment profile wherein the sheath everts such that the sheath expands in diameter relative to the maximum outer diameter in the delivery profile and shortens in length relative to the delivery profile.

2. The method of claim 1, wherein pressurizing the pressurizable chamber includes injecting a fluid between inner and outer layers to cause the sheath to evert.

3. The method of claim 2, further comprising injecting the fluid into a balloon to inflate the balloon.

4. The method of claim 3, wherein a pressure required to inflate the balloon is greater than a pressure required to cause the sheath to evert to transition to the deployment profile.

5. The method of claim 1, further comprising, after transitioning the sheath to the deployment profile, deploying the medical device without requiring further eversion of the sheath.

6. The method of claim 5, wherein the medical device is completely uncovered when the sheath is transitioned to the deployment profile.

7. The method of claim 5, wherein the medical device is configured to self-expand.

8. The method of claim 5, wherein the medical device is selected from the group consisting of stents, stent-grafts, filters, occluders, oncology therapy, valves, pressure flow monitors, indwelling catheters, drug delivery devices and wires related to the transmission of energy.

9. The method of claim 1, wherein the sheath comprises ePTFE.

10. The method of claim 9, wherein the ePTFE is anisotropic.

11. The method of claim 1, further comprising retracting a retracting member coupled to the outer layer to help evert the sheath.

12. The method of claim 11, wherein the retracting member is selected from the group consisting of a wire, a polymeric tether, and a polymeric tube.

13. The method of claim 1, wherein the inner layer is formed by inverting a portion of the sheath inwardly at a fold located on an end of the sheath, and the fold of the sheath defines a distal tip of the sheath in both the delivery profile and the deployment profile.

14. The method of claim 1, wherein the sheath is a helically wrapped or braided tubular member with an angle of wrap or braid relative to a longitudinal axis of the sheath, and the angle changes in response to the increase in the diameter of the sheath.

15. A method of delivering a medical device comprising:
positioning a radially compressed medical device within a vessel, the medical device being covered by a sheath having a delivery profile wherein the sheath is inverted to define an inner layer and an outer layer, the sheath being a helically wrapped or braided tubular member with an angle of wrap or braid relative to a longitudinal axis of the sheath, wherein a pressurizable chamber is defined between the inner and outer layers; and
pressuring the pressurizable chamber to cause the sheath to transition from the delivery profile to a deployment profile wherein the sheath everts such that the sheath expands in diameter and shortens in length relative to the delivery profile, the angle of the sheath changing in response to an increase in the diameter of the sheath.

* * * * *